(12) United States Patent
Skelton et al.

(10) Patent No.: US 9,776,008 B2
(45) Date of Patent: Oct. 3, 2017

(54) POSTURE STATE RESPONSIVE THERAPY DELIVERY USING DWELL TIMES

(75) Inventors: Dennis M. Skelton, Minneapolis, MN (US); Jon P. Davis, St. Michael, MN (US); Eric J. Panken, Edina, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1708 days.

(21) Appl. No.: 12/433,017

(22) Filed: Apr. 30, 2009

(65) Prior Publication Data

US 2010/0010381 A1    Jan. 14, 2010

Related U.S. Application Data

(60) Provisional application No. 61/080,049, filed on Jul. 11, 2008.

(51) Int. Cl.
*A61N 1/00* (2006.01)
*A61N 1/365* (2006.01)
(Continued)

(52) U.S. Cl.
CPC ........ *A61N 1/36542* (2013.01); *A61B 5/1116* (2013.01); *A61B 5/7264* (2013.01);
(Continued)

(58) Field of Classification Search
CPC ....................... A61N 1/36535; A61N 1/36542
(Continued)

(56) References Cited

U.S. PATENT DOCUMENTS 4,297,685 A    10/1981    Brainard, II
4,365,633 A    12/1982    Loughman
(Continued)

FOREIGN PATENT DOCUMENTS

DE    19831109    1/2000
DE    10024103    11/2001
(Continued)

OTHER PUBLICATIONS

"Analysis of heart rate dynamics by methods derived from nonlinear mathematics: Clinical applicability and prognostic significance," http://herkules.oulu.fi.isbn9514250133/html, 4 pp., 2004.
(Continued)

*Primary Examiner* — Nadia A Mahmood
(74) *Attorney, Agent, or Firm* — Beth L. McMahon

(57) ABSTRACT

Techniques related to classifying a posture state of a living body are disclosed. One aspect relates to sensing at least one signal indicative of a posture state of a living body. Posture state detection logic classifies the living body as being in a posture state based on the at least one signal, wherein this classification may take into account at least one of posture and activity state of the living body. The posture state detection logic further determines whether the living body is classified in the posture state for at least a predetermined period of time. Response logic is described that initiates a response as a result of the body being classified in the posture state only after the living body has maintained the classified posture state for at least the predetermined period of time. This response may involve a change in therapy, such as neurostimulation therapy, that is delivered to the living body.

57 Claims, 20 Drawing Sheets

(51) Int. Cl.
 *A61B 5/11* (2006.01)
 *A61B 5/00* (2006.01)
(52) U.S. Cl.
 CPC ............ *A61B 5/1118* (2013.01); *A61B 5/686* (2013.01); *A61B 2562/0219* (2013.01); *A61N 1/36535* (2013.01)
(58) Field of Classification Search
 USPC ........................................ 607/17, 18, 19, 62
 See application file for complete search history.

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,879,352 B1 | 4/2005 | Kim |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |

(56) References Cited

U.S. PATENT DOCUMENTS

| | | |
|---|---|---|
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 * | 12/2006 | Koh et al. ............. 607/60 |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 * | 12/2007 | Miesel ............. 607/19 |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol et al. |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth et al. |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Miesel et al. |
| 7,826,981 B2 | 11/2010 | Goode et al. |
| 8,529,448 B2 | 9/2013 | McNair |
| 8,649,862 B2 | 2/2014 | Ludwig et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0002742 A1 * | 1/2004 | Florio ............. 607/19 |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 * | 3/2005 | Singhal et al. ............. 607/19 |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0253043 A1 | 11/2006 | Zhang et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0284979 A1 * | 12/2006 | Clarkson ............. 348/143 |
| 2006/0287686 A1 | 12/2006 | Cullen et al. |
| 2007/0015976 A1 | 1/2007 | Miesel et al. |
| 2007/0032748 A1 | 2/2007 | McNeil et al. |
| 2007/0038265 A1 | 2/2007 | Tcheng et al. |
| 2007/0050715 A1 | 3/2007 | Behar |

(56) References Cited

U.S. PATENT DOCUMENTS

| | | |
|---|---|---|
| 2007/0073355 A1 | 3/2007 | DiLorenzo |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson et al. |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0106210 A1 | 4/2010 | Hedberg et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 9630079 | 10/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/87433 | 11/2002 |
| WO | 02/96512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

(56) References Cited

OTHER PUBLICATIONS

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.
Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain interrelate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media,mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48852: International Search Report and Written Opinion dated Apr. 6, 2010, 17 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.

(56) References Cited

OTHER PUBLICATIONS

U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

\* cited by examiner

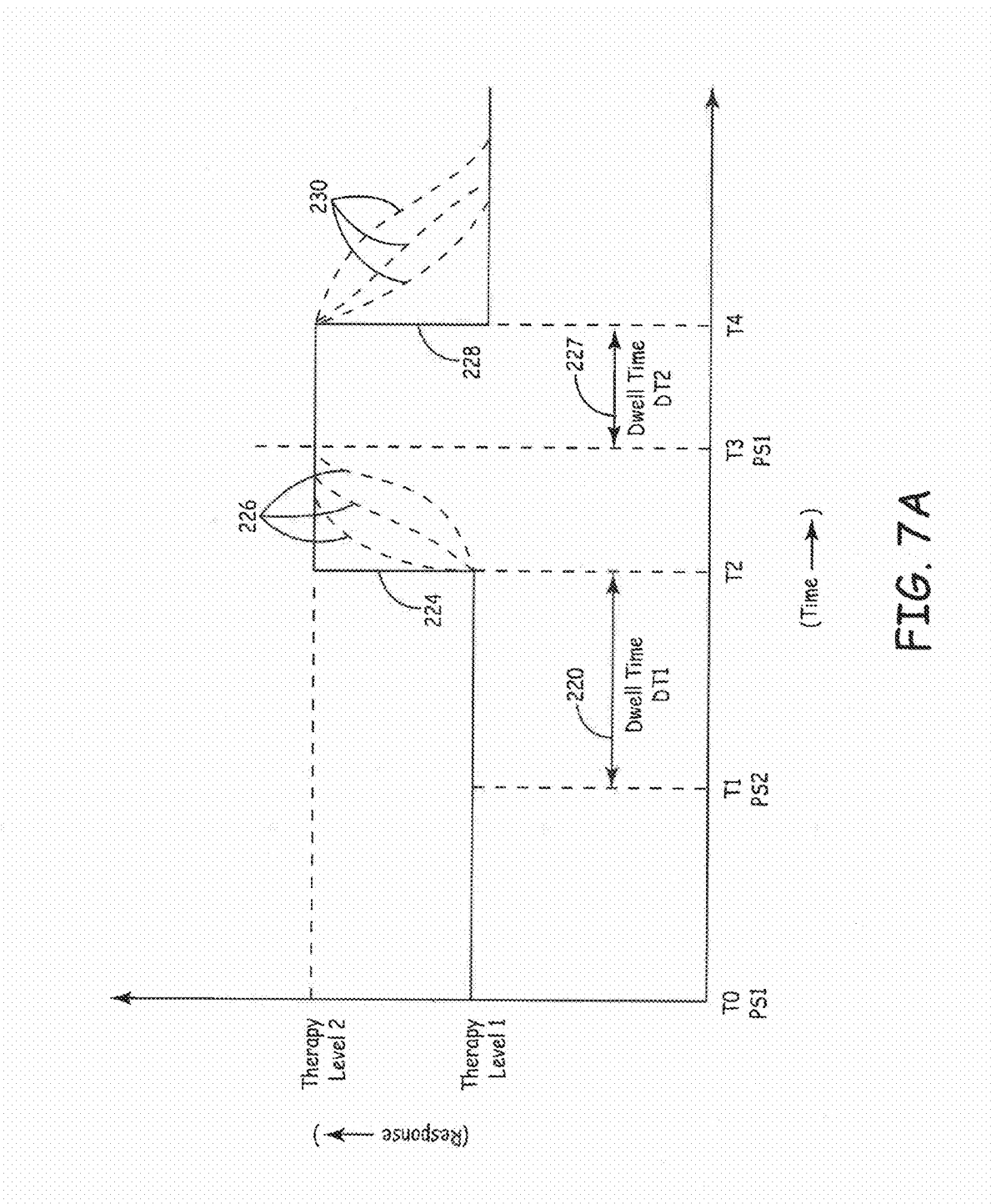

| Posture State | Response 1 - Therapy 1 | | | Response 2 - Therapy 2 | | | Response N | | |
|---|---|---|---|---|---|---|---|---|---|
| | Param 1 | Param 2 | Param N | Param 1 | ... | Param N | Param 1 | ... | Param N |
| PS1 | PA | PF | PE | PW | | PV | — | | — |
| PS2 | — | — | — | — | | — | — | | — |
| ... | | | | | | | | | |
| PSX | — | — | — | — | | — | — | | — |

| Posture State | Response Specific | | | | Change in Response | | | Physiologic Condition | | |
|---|---|---|---|---|---|---|---|---|---|---|
| | Therapy 1 | Therapy 2 | ... | Response N | Therapy Level Increase | Therapy Level Decrease | ... | Inflate Therapy | Heart Rate | Blood O₂ | Blood Pressure |

| | Posture State | Therapy 1 | Therapy 2 | ... | Response N | | | | | | |
|---|---|---|---|---|---|---|---|---|---|---|---|
| Current PS | PS1 | DT1 | DT1' | | DT1" | | | | | | |
| | PS2 | DT2 | DT2' | | DT2" | | | | | | |
| | ... | | | | | | | | | | |
| | PSX | DTX | DTX' | | DTX" | | | | | | |
| New PS | PS1 | | | | | | | | | | |
| | PS2 | | | | | | | | | | |
| | ... | | | | | | | | | | |
| | PSX | | | | | | | | | | |
| PS Transition | PS1/PS2 | | | | | | | | | | |
| | PS2/PS1 | | | | | | | | | | |
| | PS1/PSX | | | | | | | | | | |

280 — 288 — 290 — 292
282 Current PS — 284 New PS — 286 PS Transition

POSTURE STATE RESPONSIVE THERAPY DELIVERY USING DWELL TIMES

RELATED APPLICATIONS

The following application claims priority to provisionally-filed U.S. patent application entitled "Posture State Detection System and Method", patent application Ser. No. 61/080,049 filed Jul. 11, 2008, which is incorporated herein by reference in its entirety.

The following applications include some subject matter related to, or in common with, the following, each of which is incorporated herein by reference in its entirety:

"Posture State Classification for a Medical Device", U.S. patent application Ser. No. 12/433,004, filed on even date herewith;

"Posture State Classification for a Medical Device", U.S. patent application Ser. No. 12/432,993, filed on even date herewith;

"Reorientation of Patient Posture States for Posture-Responsive Therapy", U.S. patent application Ser. No. 12/433,623, filed on even date herewith; and "Posture State Detection Using Selectable System Control Parameters", U.S. patent application Ser. No. 12/433,029, filed on even date herewith.

TECHNICAL FIELD

The disclosure relates to posture detection techniques, and more particularly, to medical devices that deliver therapy in response to detection of posture states.

BACKGROUND

A variety of types of medical devices are used for chronic, e.g., long-term, provision of therapy to patients. As examples, pulse generators are used for provision of cardiac pacing and neurostimulation therapies, and pumps are used for delivery of therapeutic agents, such as drugs. Typically, such devices provide therapy continuously or periodically according to parameters. For instance, a program comprising respective values for each of a plurality of parameters may be specified by a clinician and used to deliver the therapy.

It may be desirable in some circumstances to activate and/or modify the therapy based on a patient state. For example, the symptoms such as the intensity of pain of patients who receive spinal cord stimulation (SCS) therapy may vary over time based on the activity level or posture of the patient, the specific activity undertaken by the patient, or the like. It is desirable to be able to detect and classify the state of the patient accurately so that this classification may be used to activate and/or select a therapy that is most efficacious for that state.

SUMMARY

According to the disclosure, posture classification may, in one embodiment, be performed by first creating posture definitions that describe postures a patient may assume. Once such definitions are created, signals obtained from a sensor that describe the patient's current posture may be compared with one or more other signal levels that have been associated with the defined postures. If this comparison indicates that the signals obtained from the sensor have a predetermined relationship to signal values associated with a defined posture, the patient's posture may be classified according to that defined posture. Some action may then be initiated in response to this posture classification. For instance, therapy may then be delivered to the patient using therapy parameters that have previously been associated with the posture in which the patient is currently being classified. Alternatively or additionally, some other action may be taken, such as providing a notification (e.g., indicating a potential fall), initiating the storing of data, and so on.

In a similar manner, aspects of the current disclosure relate to classifying a patient's activity state, and then delivering therapy or performing some other action based on that classification. A patient's activity state relates to the motion or activity of the patient. The activity state may describe, for example, an overall activity level (e.g., footfalls), an activity level in one or more selected directions, a vector associated with velocity or acceleration of motion, and so on. To classify a patient's activity state, signals indicative of that activity state may be compared to signal values associated with activity state definitions. Based on this comparison, therapy parameters may be selected for use in delivering therapy to a patient. Alternatively or additionally, some other action may be taken based on this comparison.

In the foregoing manner, a patient's posture state may be classified, wherein the posture state classification takes into account at least one of the classification of the patient's posture and the classification of the patient's activity state. According to the current disclosure, it may be desirable to ensure that a patient's posture state classification is stable before some action is taken in response to the classification. For instance, after a patient is classified in a posture state P and before a change in therapy is initiated in response to this classification, it may be desirable to require the expiration of a time delay T. If the patient's posture state does not remain classified as posture state P during the duration of time T, the change to the therapy that has been associated with this posture state will not be initiated. This time delay, which may be referred to as a dwell time, is used to prevent posture states that are only temporarily assumed from affecting therapy, or from initiating some other action. In other words, only those posture states that are assumed by a patient for some required length of time will result in the initiation of some action. The dwell time period may be programmable and/or may be based on conditions monitored within the system.

Another type of stability technique that may be employed in a posture state classification system involves that associated with episode detection. According to episode detection, a level of a signal indicative of posture or activity is monitored. This signal level must cross a transition threshold level that has been associated with the episode. Once this crossing occurs, the signal level must not re-cross the transition threshold level in an opposite direction for a length of time, referred to as a transition duration, which has been associated with the episode detection. If such a re-crossing occurs, a change in the patient's posture or activity state will not be recognized. As with dwell times, the use of episode detection introduces stability into the system, since it prevents recognition of activity state or posture changes that are only transitory, and should not be used to initiate a response. This prevents multiple therapy changes from being initiated in close succession in response to a posture state that is hovering near a transition area. In some embodiments, the transition duration and transition threshold may be programmable, and/or may be automatically selected based on monitored system conditions, which may involve a current posture and/or activity state.

According to another aspect, an M-of-N filter may be employed to ensure that transitional posture state changes do not initiate an unwanted response. According to this technique, a particular posture state must be detected during M of the last N sample time periods before this posture state will be employed for use in classifying a patient's posture state. This type of filter reduces the chances that a transitory posture state will be used to initiate an unwanted response. In some embodiments, the values for M and N may be programmable, and/or may be automatically selected based on monitored system conditions, which may involve a current posture and/or activity state.

One aspect of the disclosure relates to a system that includes a sensor that senses at least one signal indicative of a posture state of a living body, and posture state detection logic that classifies the living body as being in a posture state based on the at least one signal. The posture state detection logic further determines whether the living body is classified in the posture state for at least a predetermined period of time. Response logic is described that initiates a response as a result of the body being classified in the posture state only after the living body has maintained the classified posture state for at least the predetermined period of time.

Another embodiment relates to a medical system to provide therapy to a living body. The system includes a sensor, posture state detection logic receiving at least one signal from the sensor and employing the at least one signal to classify a posture state of the living body, and a therapy module. The therapy module controls the therapy provided to the living body based on the classification. A programmer is provided to program the posture state detection logic to determine whether, after the living body is classified in a posture state, the living body maintains the posture state for a predetermined period of time, and if so, to provide an indication to allow the therapy module to adjust the therapy in response to the posture state, and otherwise, to allow the therapy to remain unchanged.

According to another aspect of the disclosure, a method is provided that includes receiving at least one signal from a sensor, classifying a living body as being in any of multiple defined posture states based on the at least one signal, and determining whether the living body is classified in a same posture state for a predetermined period of time. If the living body is classified in the same posture state for the predetermined period of time, a response is initiated that is determined based on the posture state.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 7A is a timing diagram illustrating use of dwell times according to one exemplary embodiment of the disclosure.

FIG. 8 is an exemplary data structure that may be employed to associate posture states with responses.

FIG. 9 is an exemplary data structure that may be employed to select dwell times according to one embodiment of the disclosure.

DETAILED DESCRIPTION

Figure 1:
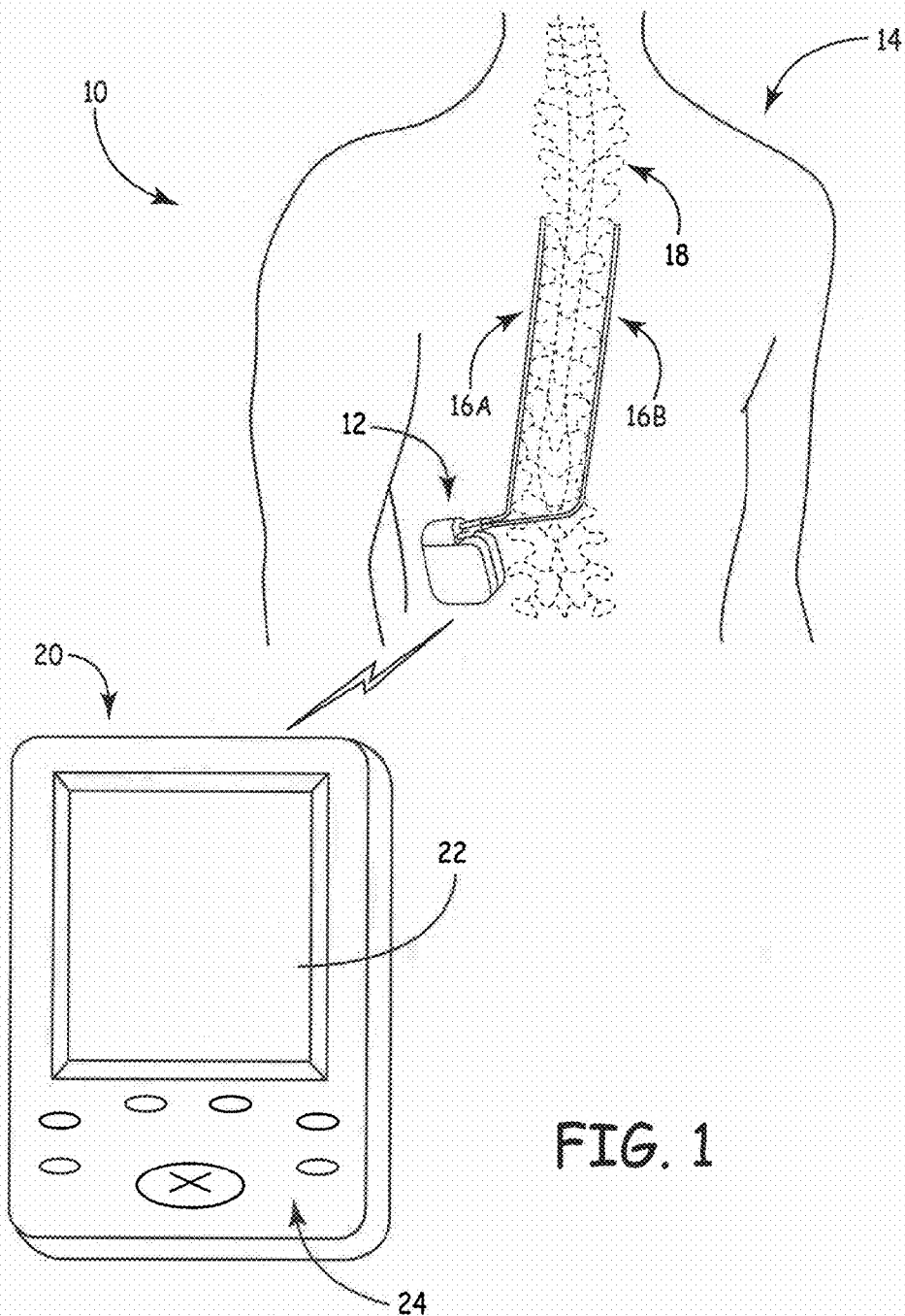
FIG. 1 is a conceptual diagram illustrating an example system that facilitates the definition and classification of posture states according to the disclosure.

Techniques described herein relate to using one or more signals from a sensor to classify a patient's posture and/or activity state. As used herein, "signal" refers to a logical signal, as may be described by logic levels transmitted on one or more physical connections of an interface in parallel or in series. For instance, a signal may be described by voltage or current levels transmitted in parallel on a multi-line interface, or in series on a single-line interface.

According to the disclosure, posture classification may, in one embodiment, be performed by first creating posture definitions that describe postures a patient may assume. Once such definitions are created, signals obtained from a sensor that describe the patient's current posture may be compared with one or more other signal levels that have been associated with the defined postures. If this comparison indicates that the signals obtained from the sensor have a predetermined relationship to signal values associated with a defined posture, the patient's posture may be classified according to that defined posture. Some action may then be initiated in response to this posture classification. For instance, therapy may then be delivered to the patient using therapy parameters that have previously been associated with the posture in which the patient is currently being classified. Alternatively or additionally, some other action may be taken, such as providing a notification (e.g., indicating a potential fall), initiating the storing of data, and so on.

In a similar manner, aspects of the current disclosure relate to classifying a patient's activity state, and then delivering therapy or performing some other action based on that classification. A patient's activity state relates to the motion or activity of the patient. The activity state may describe, for example, an overall activity level (e.g., footfalls), an activity level in one or more selected directions, a vector associated with velocity or acceleration of motion, and so on. To classify a patient's activity state, signals indicative of that activity state may be compared to signal values associated with activity state definitions. Based on this comparison, therapy parameters may be selected for use in delivering therapy to a patient. Alternatively or additionally, some other action may be taken based on this comparison.

Posture definitions and activity state definitions may each be described as being a subset of a more general class of definitions referred to as posture state definitions. A posture state definition may specify a posture, an activity state, or both. According to a general approach, signals describing either a patient's posture, activity state, or both, may be compared to signal values included in posture state definitions. The patient's posture state may be classified based on this comparison so that therapy may be delivered to a patient according to therapy parameter values associated with the classified posture state definition. Alternatively, or additionally, some other type of action may be taken in response to this classification, such as providing a notification, initiating recording of data, initiating a communication session with an external device, and so on.

According to the current disclosure, it may be desirable to ensure that a patient's posture state classification is stable before some action is taken in response to the classification. For instance, after a patient is classified in a posture state P and before a change in therapy is initiated in response to this classification, it may be desirable to require the expiration of a time delay T. If the patient's posture state does not remain classified as posture state P during the duration of time T, the change to the therapy that has been associated with this posture state will not be initiated. This time delay, which may be referred to as a dwell time, is used to prevent posture states that are only temporarily assumed from affecting therapy, or from initiating some other action. In other words, only those posture states that are assumed by a patient for some required length of time will result in the initiation of some action. The dwell time period may be programmable and/or may be based on conditions monitored within the system.

Another type of stability technique that may be employed in a posture state classification system involves that associated with episode detection. According to episode detection, a level of a signal indicative of posture or activity is monitored. This signal level must cross a transition threshold level that has been associated with the episode. Once this crossing occurs, the signal level must not re-cross the transition threshold level in an opposite direction for a length of time, referred to as a transition duration, which has been associated with the episode detection. If such a re-crossing occurs, a change in the patient's posture or activity state will not be recognized. As with dwell times, the use of episode detection introduces stability into the system, since it prevents recognition of activity state or posture changes that are only transitory, and should not be used to initiate a response. This prevents multiple therapy changes from being initiated in close succession in response to a posture state that is hovering near a transition area. In some embodiments, the transition duration and transition threshold may be programmable, and/or may be automatically selected based on monitored system conditions, which may involve a current posture and/or activity state.

According to another aspect, an M-of-N filter may be employed to ensure that transitional posture state changes do not initiate an unwanted response. According to this technique, a particular posture state must be detected during M of the last N sample time periods before this posture state will be employed for use in classifying a patient's posture state. This type of filter reduces the chances that a transitory posture state will be used to initiate an unwanted response. In some embodiments, the values for M and N may be programmable, and/or may be automatically selected based on monitored system conditions, which may involve a current posture and/or activity state.

Examples of therapies that may be delivered in a closed-loop manner according to the present disclosure include electrical stimulation or the delivery of therapeutic agents. Electrical stimulation may be, for example, used to treat patients that suffer from chronic back pain, leg pain, or other pain that cannot be treated through other methods. As a patient changes posture state, which may involve changes in position and/or activity level, the stimulation may need to be adjusted in order to maintain efficacy. Such changes in a patient's posture state may be detected, classified, and used to modify a therapy that is currently being delivered, or select a new therapy for delivery to the patient. Other types of therapies, such as drug delivery therapy, may be modified in a similar manner in response to detected posture state transitions. In another embodiment, the detected posture state transitions may be used to prompt some notification, or to record some information.

According to some embodiments of the disclosure, a patient's posture state is sensed using signals obtained from a sensor. This sensor may be housed within an implantable medical device (IMD), or may be communicatively or otherwise coupled to the IMD. The sensor may be a three-axis accelerometer such as a piezoelectric and/or micro-electro-mechanical (MEMs) accelerometer. The sensed signals may be used to classify a posture state that is then employed to determine a therapy adjustment.

FIG. 1 is a conceptual diagram illustrating an example system 10 that facilitates the definition and classification of posture states according to the disclosure. These posture states may then be utilized to deliver therapy to a patient. In the illustrated example, system 10 includes an IMD 12, which is implanted within a patient 14, and delivers neurostimulation therapy to patient 14.

IMD 12 delivers neurostimulation therapy to patient 14 via therapy connections 16A and 16B (collectively "therapy connections 16"), which may be leads, catheters, or some other type of therapy delivery device. Therapy connections 16 may, as shown in FIG. 1, be leads implanted proximate to the spinal cord 18 of patient 14, and IMD 12 may deliver SCS therapy to patient 14 in order to, for example, reduce pain experienced by patient 14. In another embodiment, such stimulation may be delivered to areas around the spine to provide cardioprotection related to detection of onset of ischemia. In still another embodiment, such stimulation may be provided in relation to heart failure. In yet another scenario, one or more leads may extend from IMD 12 to the brain (not shown) of patient 14, and IMD 12 may deliver deep brain stimulation (DBS) therapy to patient 14 to, for example, treat tremor, Parkinson's disease, or epilepsy. As further examples, one or more leads may be implanted proximate to the pelvic nerves, stomach, or other organs (not shown) and IMD 12 may deliver neurostimulation therapy to treat incontinence, gastroparesis, sexual dysfunction or other disorders. In another embodiment, IMD 12 may be a device other than a neurostimulator, such as a cardiac therapy device to deliver stimulation to the heart.

Further, as discussed above, the disclosure is not limited to embodiments in which IMD 12 delivers stimulation therapy. For example, in some embodiments, IMD 12 may additionally or alternatively be coupled to one or more catheters or other substance delivery devices to deliver one or more therapeutic substances to patient 14, e.g., one or more drugs. Also, in some aspects, techniques for evaluating postures and activity states as described herein may be applied to IMDs that are generally dedicated to sensing or monitoring and do not include stimulation or other therapy components.

Additionally, this disclosure is not limited to implanted devices. Any implantable or external medical device may classify posture states for use in delivering therapy according to the techniques described herein. Moreover, these techniques may also be used for purposes other than delivering therapy. For instance, the posture state detection mechanisms described herein may be used for diagnostic purposes, such diagnosing a need for therapy, or determining how a patient is responding to existing therapy. Posture state detection may also be used to provide notifications, such as providing notification via a wireless link to a care giver that a patient has potentially experienced a fall. Thus, posture definition and classification according to the current disclosure may be used to initiate many types of actions.

In exemplary embodiments, IMD 12 may initiate actions in response to information within a record. For instance, a plurality of records may be stored in a table or another data structure. Each such record may describe at least one posture state and an associated action that is to be taken in response to detection of this posture state. As discussed above, a posture state is determined based on at least one of a posture and an activity state. When IMD 12 detects that a patient is in some predefined posture state, IMD 12 may automatically initiate the associated action for that posture state. This action may involve delivery of therapy according to a particular program, group of programs and/or a set of parameters. This action may alternatively or additionally involve providing some notification, initiating a communication session with an internal or external device, and/or recording some information. Other types of responses are possible.

In the illustrated example, system 10 also includes a programming device 20, which may, as shown in FIG. 1, be a handheld computing device. Programming device 20 allows a user such as a patient or a clinician to interact with IMD 12. Programming device 20 may, for example, communicate via wireless communication with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a clinician programmer used by a clinician to define postures and posture states according to the current disclosure. The defined postures may then be used to detect postures, activity states, and posture states that are assumed by the patient during daily life. The detected conditions may be used to determine a type of therapy to provide to the patient, to monitor general well-being of the patient, to prescribe new therapies for the patient, to determine whether the patient has undergone a posture-specific event such as suffering a fall and/or to initiate other types of actions.

Figure 2:
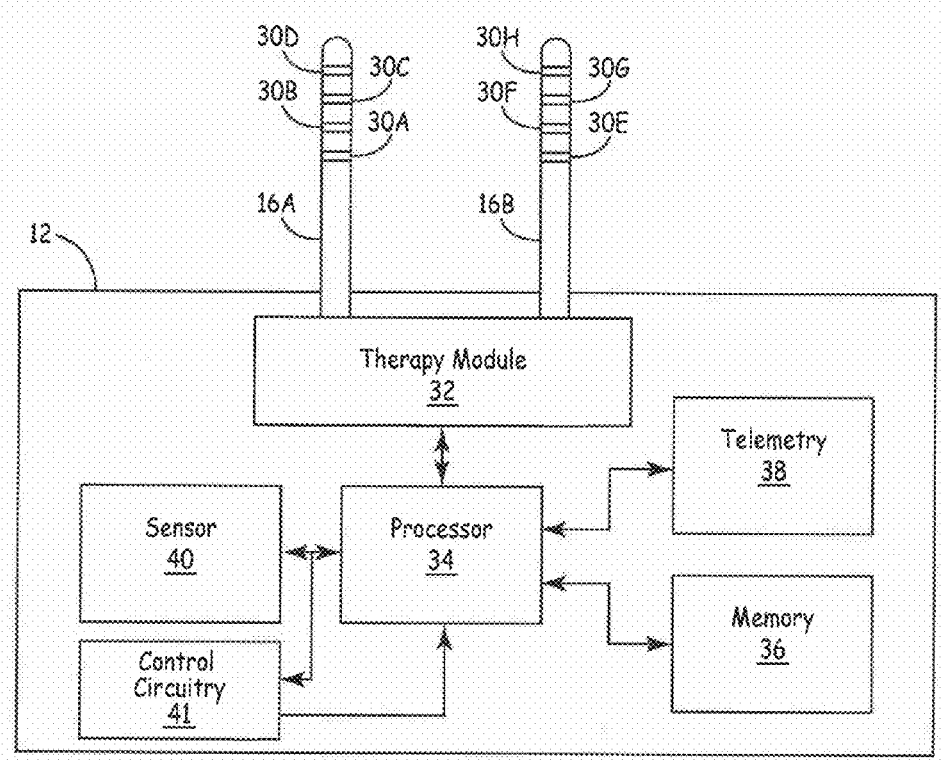
FIG. 2 is a block diagram illustrating one embodiment of an Implantable Medical Device (IMD) in greater detail.

FIG. 2 is a block diagram illustrating one embodiment of IMD 12 in greater detail. IMD 12 may deliver neurostimulation therapy via therapy connections 16A and 16B. These therapy connections are shown to be leads having one or more electrodes 30A-H (collectively "electrodes 30"). They may alternatively include some other devices, such as one or more catheters for delivering a substance to a patient. IMD 12 may be coupled to any number of therapy connections. Therapy connections 16A and 16B are coupled to IMD 12 via therapy module 32. This may be a stimulation pulse generator, for example. Such a pulse generator may be coupled to a power source such as a battery. Therapy module 32 may deliver electrical pulses to patient 14 and/or may deliver some type of substance, such as a drug.

Therapy delivery may occur under the control of a processor 34. Processor 34 may comprise a microprocessor, a controller, a digital signal processor (DSP), an application specific integrated circuit (ASIC), a field-programmable gate array (FPGA), discrete logic circuitry, or any combination thereof.

Processor 34 may control therapy module 32 to deliver neurostimulation or other therapy according to a selected program. For instance, processor 34 may control therapy module 32 to deliver electrical pulses with amplitudes, widths, and/or at rates specified by the program. Processor 34 may also control therapy module 32 to deliver such pulses via a selected subset of electrodes 30 with selected polarities, e.g., a selected electrode configuration, as specified by the program.

IMD 12 also includes a telemetry circuit 38 that allows processor 34 to communicate with programming device 20. For example, a clinician may select programs, parameters, posture definitions, activity state definitions, other posture state definitions, and associated therapies and actions that are to be transferred to memory 36 of IMD 12. Processor 34 also communicates with programming device 20 to provide diagnostic information stored in memory 36 to a clinician via telemetry circuit 38. Processor 34 may also communicate with a patient programming device to receive therapy parameter adjustments or other therapy adjustments from a user such as patient 14, as well as commands to initiate or terminate stimulation. Telemetry circuit 38 may correspond to any telemetry circuit known in the implantable medical device arts.

IMD 12 further includes a sensor 40 to sense one or more parameters used to detect a posture state. In exemplary embodiments, sensor 40 includes a three-axis accelerometer, such as a piezoelectric and/or MEMs accelerometer. In other embodiments, multiple single or multi-axis accelerometers may be employed in place of one three-axis accelerometer. In yet other examples, sensor 40 may include gyroscopes or other sensors capable of sensing posture and/or activity levels. Thus, it will be understood that sensor 40 may comprise more than one sensor.

In exemplary embodiments, sensor 40 is located within a housing (not shown) of IMD 12. However, the disclosure is not so limited. In some embodiments, sensor 40 is coupled to IMD 12 via one or more additional connections such as leads (not shown). The sensor may be located anywhere within patient 14. In some embodiments, IMD 12 may be coupled to multiple sensors located at various positions within patient 14 or on the external surface of patient 14, and processor 34 may receive more detailed information about the posture of, and activity undertaken by, patient 14. For example, one or more accelerometers may be located within/on the torso and at a position within/on a limb, e.g. a leg, of patient 14. In yet other embodiments, these one or more sensors may communicate wirelessly with IMD 12 instead of requiring one or more leads to communicate with the IMD. For example, sensor 40 may be located external to patient 12 and may communicate wirelessly with processor 34, either directly or via programming device 20.

As previously mentioned, sensor 40 senses one or more parameters that are used to detect and classify a posture state. A posture state is based on at least one of a posture and an activity state of a patient, where the activity state describes motion or activity of the patient. The activity state may relate to an overall activity level, an activity level in one or more selected directions, a vector associated with velocity or acceleration, and so on.

As an example, an Upright posture state may be defined to classify the position of a patient who is standing. This posture state definition need not take into account the patient's activity state, if desired. As another example, an Upright and Active posture state may be defined to describe a patient who is standing and who has undertaken an activity level that exceeds some predetermined threshold level. As yet another illustration, an Active posture state may be defined to describe a patient who exceeds some level of activity without regard to the posture that patient assumes during this activity. In this manner, sensor 40 may be used to detect a posture state associated with various types of postures and/or activity states.

IMD 12 also includes a memory 36, which may store programmed instructions that, when executed by processor 34, cause IMD 12 to perform the functions ascribed to IMD 12 herein. Memory 36 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

FIG. 2 may further include control logic 41. This control logic is provided in one embodiment to obtain and process the analog output of sensor 40. Control logic 41 may include discrete components, a microprocessor, a controller, a digital signal processor (DSP), an application-specific integrated circuit (ASIC), a field-programmable gate array (FPGA), programmed instructions executable by one or more processors, or the like. Control logic 41 may operate alone, or in conjunction with processor 34, to process the sensor output for use in detecting a posture state. As an example, control logic 41 may process the raw signals provided by sensor 40 to determine activity counts indicative of activity level, velocity along one or more accelerometer axis, and so on, for use in detecting a posture state. As previously indicated, at least some of this processing may be carried out by processor 34 under control of programs stored within memory 36. Thus, control logic 41 may comprise any combination of hardware and/or programmed instructions.

Figure 3:
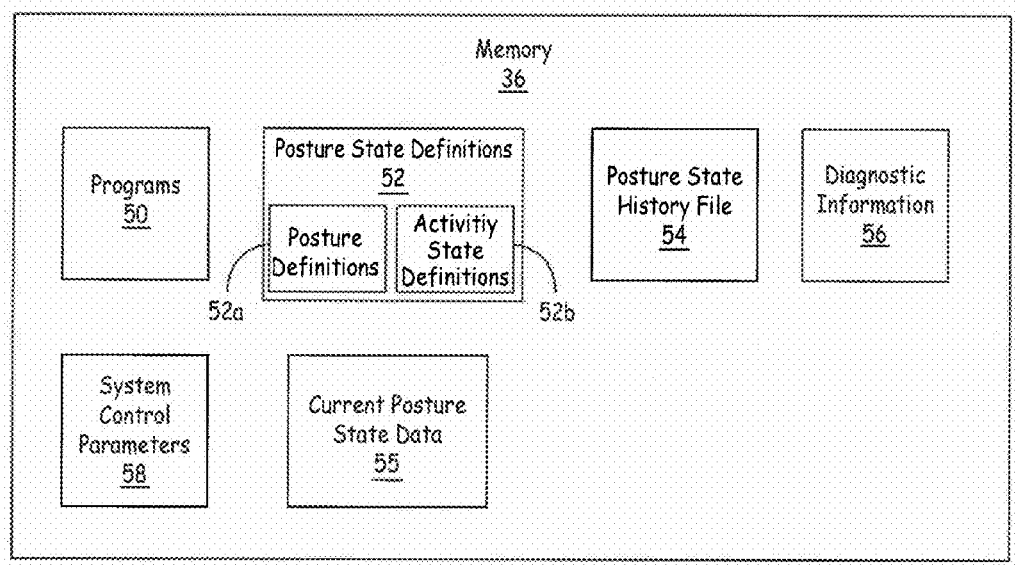
FIG. 3 is a block diagram illustrating an exemplary configuration of a memory of an Implantable Medical Device (IMD) according to an embodiment of the disclosure.

FIG. 3 is a block diagram illustrating an exemplary configuration of memory 36 of IMD 12. As illustrated in FIG. 3, memory 36 stores programs 50, one or more of which processor 34 may employ to control therapy that is delivered to the patient. Some of programs 50 may be provided to take actions in response to classification of a patient's posture state. Programs 50 may also include those for controlling various aspects of processing signals of sensor 40 according to techniques described herein.

Memory 36 further stores posture definitions 52a and activity state definitions 52b, each of which is a subset of posture state definitions 52. In particular, a posture definition is a posture state definition that is defined only in terms of a patient's posture without regard to activity. An activity state definition is a posture state definition that is defined only in terms of a patient's activity without regard to posture. Other types of posture state definitions are defined in terms of both activity and posture.

A record of the posture states that have been assumed by the patient over time may be recorded in a posture state history file 54. In conjunction with this history file, information concerning the patient's current posture state may be maintained as current posture state data 55. This data may record, for instance, the patient's current posture, current activity state, or both.

Memory 36 may also store diagnostic information 56 for use in determining how a patient is responding to therapy, whether therapy modification is needed, whether therapy is to be initiated, and so on.

In one embodiment, system control parameters 58 may also be stored in memory 36. These parameters may be used to control, among other things, how signals from sensor 40 should be obtained and processed to classify a patient's posture state. These system control parameters 58 may, in one embodiment, be selected based on current posture state data 55. For instance, the parameters in use at a given time may be selected based on the posture state in which the patient was most recently classified.

According to the current disclosure, system control parameters 58 may store one or more dwell times, which are delay times imposed between the time a patient is classified in a posture state, and the time an action is taken in response to this detected posture state. If the patient exits this posture state at any time throughout the dwell time, the one or more actions associated with this posture state will not be initiated. This use of a dwell time introduces stability into the system, since temporarily assumed activity states do not result in the initiation of any action.

In one embodiment, dwell times may be programmable. Moreover, a dwell time that is in use within the system may be automatically selected based on the newly-assumed posture state that triggered the use of the dwell time, the patient's most-recent stable posture (which, in one embodiment, may be identified by current posture state data 55), the specific transition from the most-recent stable posture state to the newly-assumed posture state, or some other condition that is sensed within the system. This will be discussed below.

Values that control M-of-N filter processing may likewise be stored as system control parameters 58. These values may include one or more values to be used as M and/or N.

Likewise, values that control episode detection, including transition durations and transition thresholds, may be stored as system control parameters 58. Any or all of these values may be programmable. Moreover, the values in use at any given time may be automatically selected in the manner described above with respect to dwell times.

Figure 4A:
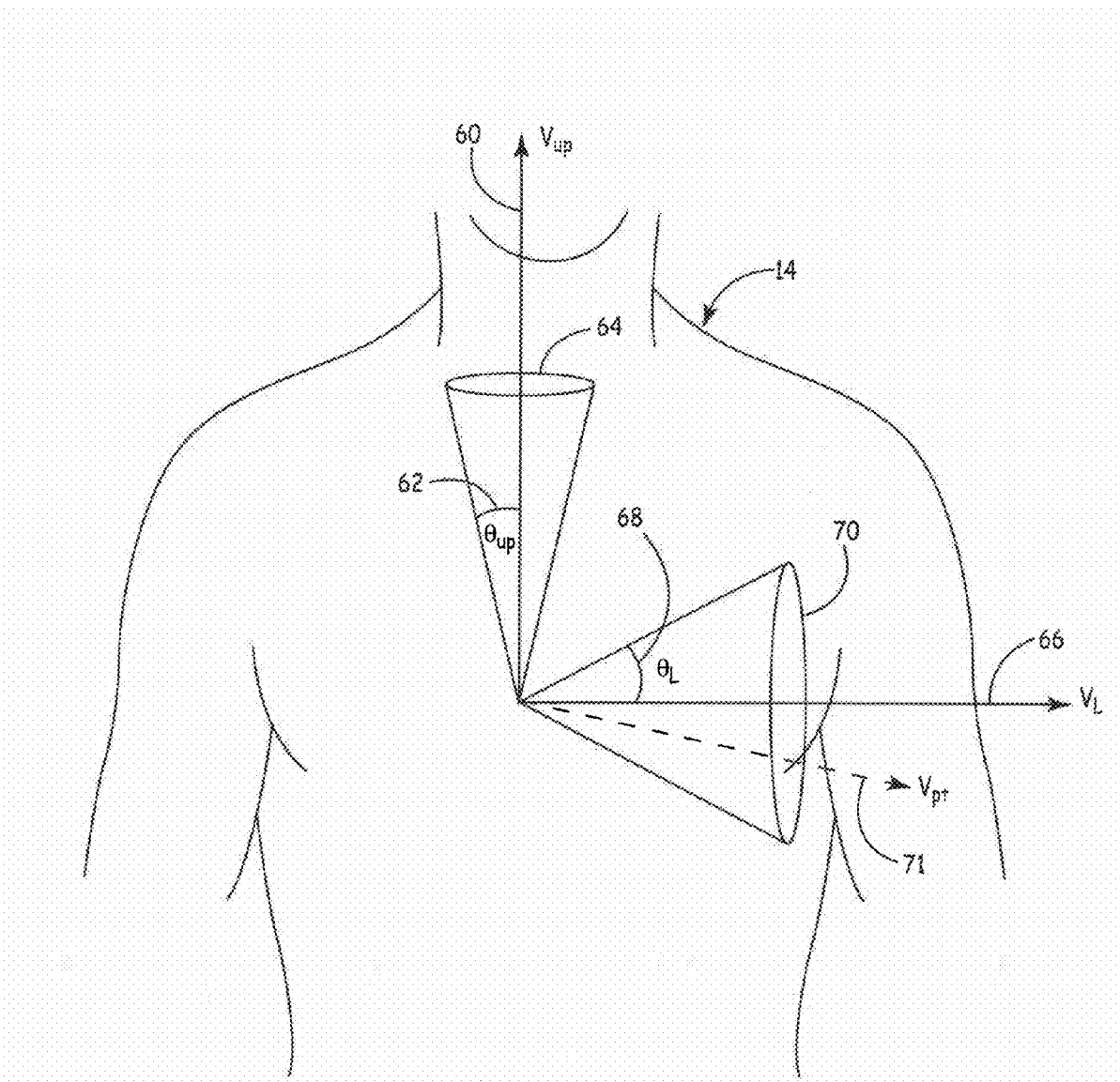
FIG. 4A is a conceptual diagram illustrating defining and classifying postures according to the current disclosure.

FIG. 4A is a conceptual diagram illustrating one exemplary method of defining and classifying postures using sensor 40. Sensor 40 (not shown) is disposed in a fixed manner relative to patient 14. When patient 14 is known to be standing upright, sensor 40 will provide outputs that can be processed to obtain a vector [$V_1, V_2, V_3$] which is shown as $V_{Up}$ 60. This vector $V_{Up}$ may be referred to as a defined posture vector, since it will be associated with a defined posture during a posture definition process, as by storing some indication of the Upright posture along with one or more values identifying this defined posture vector $V_{Up}$. A tolerance may also be selected for this defined posture that describes a distance relationship to vector $V_{Up}$ 60. In the current example, the tolerance is an angle $\theta_{Up}$ 62 which may identify a maximum distance from vector $V_{Up}$ in any direction, as illustrated by cone 64. The vector $V_{Up}$ 60, which may be referred to as a defined posture vector, as well as the selected tolerance, which in this case is angle $\theta_{Up}$ 62, may be stored (e.g., in memory 36) in association with an indicator identifying the Upright posture. This information may be stored as one of posture definitions 52a, for instance.

Once created in the foregoing manner, the definition for the Upright posture may be used to classify a patient's posture as follows. As the patient goes about daily life, one or more signals from sensor 40 may be acquired and optionally processed. Such processing may, for example, retain DC portions of the sensor signals for use in classifying a patient's posture. These signals may then be used to obtain a vector describing the patient's current posture. Such a vector may be referred to as a detected posture vector $V_{pt}$. This detected posture vector may be compared to defined posture vectors of posture definitions. For instance, this detected posture vector $V_{pt}$ that describes the patient's current posture may be compared to defined posture vector $V_{Up}$ for an Upright posture.

If a comparison between a detected posture vector $V_{pt}$ and a defined posture vector indicates that the detected posture vector satisfies the tolerance relationship indicated by the definition for the Upright posture, the patient will be considered to be in the Upright posture. For instance, in this case, if it is determined that the detected posture vector $V_{pt}$ lies within the cone 64 for the Upright posture as determined by the selected tolerance angle of $\theta_{Up}$ 62, the patient is classified as being in the Upright posture. This determination may be made using angles, similarity metrics that may include trigonometric relationships (e.g., sine, cosine), other similarity metrics that involve other distance relationship such as city-block distances, and so on. According to this example, the patient may be leaning slightly forward, backward, or to either side of, vector $V_{Up}$, while still being categorized as being in the Upright posture so long as the detected posture vector lies within cone 64 defined by angle $\theta_{Up}$ 62.

In the specific examples of FIG. 4A, the patient is classified as being in a posture if the detected posture vector $V_{pt}$ lies within an associated cone. In other examples, a patient may be classified as being in a posture if it is determined that a detected posture vector $V_{pt}$ lies outside of a cone that surrounds a defined posture vector. As previously described, these determinations may utilize angle comparisons, or similarity metrics involving trigonometric functions (e.g., sine, cosine), other distance relationship comparisons, and so on.

Example methods of comparing a detected posture vector to defined posture vectors are provided in commonly-assigned patent applications entitled "Posture State Detection System and Method", U.S. Patent Application No. 61/080,049 and Ser. No. 12/433,004, referenced above. The specific methods of comparing a detected posture vector to defined posture vectors are largely outside of the scope of the current disclosure, and other methods of using a vector to determine a patient's posture will be contemplated by those skilled in the art.

In a similar manner, other posture vectors may be defined. For instance, a vector $V_L$ 66 may be defined that will be used to determine a Left Side posture in which the patient 14 will be classified when he is lying on his left side. In a manner similar to that described above, a tolerance is defined for this vector that involves an angle $\theta_L$ 68. This angle may be used to describe a cone 70 defining a maximum distance from $V_L$ 66. When a detected posture vector lies within this posture cone 70, the patient 14 will be classified as lying on his left side.

In the foregoing manner, any one or more defined posture vectors may be selected for use in creating a posture definition. The posture definitions may each be associated with defined posture vectors that need not be in any particular plane or have in any relationship to any other posture vector.

As previously discussed, in one embodiment, posture definitions may be created using patient participation. For instance, a patient may be requested to assume a posture, such as lying on his left side. While this posture is maintained, signals from sensor 40 may be obtained and processed in a certain manner. The resulting signal levels may be stored as a vector that is associated with a selected one of the posture definitions 52a, such as Left Side. The capture and storing of signals in this manner may be initiated by a user such as a clinician who is employing a user interface of programmer 20 (FIG. 1), for instance. The user may further employ programmer 20 to select a tolerance. For instance, this tolerance may indicate the size of $\theta_L$ as well as specify that the detected posture vector must lie within the cone defined by the angle in order for the patient to be classified in this posture. In this manner, patient participation may be used to create a posture definition.

In other embodiments, one or more posture definitions may be pre-defined and pre-stored within an IMD or another device without use of patient participation. For instance, a device manufacturer or a clinician may create these definitions by selecting a vector and tolerance without the aid of the patient. These selected values may then be associated with a posture definition. Exemplary methods for generating and re-orienting posture definitions and posture state definitions are provided in commonly-assigned Patent Applications entitled "Reorientation of Patient Posture States for Posture-Responsive Therapy", U.S. application Ser. No. 12/433,623, and "Posture State Classification for a Medical Device", U.S. patent application Ser. Nos. 12/433,004 and 12/432,993, referenced above.

As may be appreciated, posture in which a patient will be classified will change as the patient goes about daily life. For instance, when a patient is in an upright position such that the detected posture vector $V_{pt}$ 71 lies within cone 64 associated with the Upright posture, the patient's posture will be classified as being in the Upright posture. If the patient transitions from the upright position to lying on his left side, the detected posture vector $V_{pt}$ 71 will transition from being located within cone 64 into the space that is not associated with any posture state definition. From there, the detected posture vector $V_{pt}$ 71 will transition into cone 70 associated with the Left Side posture.

According to the current example, the patient may be receiving some therapy associated with the Upright posture while the detected posture vector $V_{pt}$ 71 resides within cone 64. This therapy may optionally continue as detected posture vector $V_{pt}$ enters the space that is not associated with any defined postures or some other therapy may be delivered during this time. In one embodiment, some change in therapy may be initiated as the detected posture vector $V_{pt}$ 71 enters cone 70 associated with the Left Side posture. Thus, a change in therapy may be initiated as the patient's posture is re-classified. Alternatively or additionally, some other action may be taken as a result of this posture re-classification.

As previously discussed, a dwell time may be imposed between the time the patient's posture state is re-classified and the time a response is initiated as a result of this re-classification. This dwell time may, if desired, be programmable. In one embodiment, the dwell time may be selected based on the patient's previous posture classification (in this example, the Upright posture classification). In another embodiment, the dwell time may be selected based on the newly-assumed posture (in this example, the Left Side posture). In yet another embodiment, this dwell time may be selected based on the particular posture transition (e.g., Upright to Left Side) that was experienced by the patient. According to another aspect, the dwell times may further be specific to a particular type of response or action that is to be initiated. Other conditions may be used to select the dwell time, as will be discussed below.

This use of dwell time stabilizes the system by ensuring that temporarily-assumed posture states do not initiate a response. Thus, if the detected posture is only transitory, as may be the case if a patient is transitioning to a final posture by assuming one or more temporarily postures, the temporarily-assumed postures will not cause delivered therapy to be adjusted in an unwanted manner. Moreover, if the patient aborts the posture transition, as by changing his or her mind mid-way through a transition, the aborted transition likewise will not prompt a therapy change.

If desired, a dwell time may be selected that is specific to a particular response. As an example, upon entry of the Left Side posture, more than one response may be initiated. One such response may involve alteration of a therapy parameter (e.g., increase or decrease of an amplitude involving delivery of stimulation therapy). Another response may involve initiation of a different therapy (e.g., initiation of administration of a therapeutic substance to the patient). Yet another response may involve providing some type of notification to an external device such as a patient or clinician programmer, or a notification to the patient himself, as by the IMD generating a tone, vibration, or stimulation pattern that may be perceived by the patient. In one embodiment, for each such response that is to occur as a result of the newly-detected posture, a different dwell time may be imposed. Thus, dwell times may, if desired, be response-specific.

As is the case with dwell times, use of episode detection and/or of an M-of-N filter may be employed to introduce stability into the system, and prevent temporarily-assumed postures from resulting in the initiation of unwanted actions. This is discussed further below.

The foregoing provides some examples of how one or more signals from sensor 40 may be obtained and used as a detected posture vector $V_{pt}$ to classify a patient's posture and initiate some response. In a similar manner, signals from a sensor 40 may be used to classify a patient's activity state. This activity state may be used alone or in conjunction with a detected posture to initiate some response.

Figure 4B:
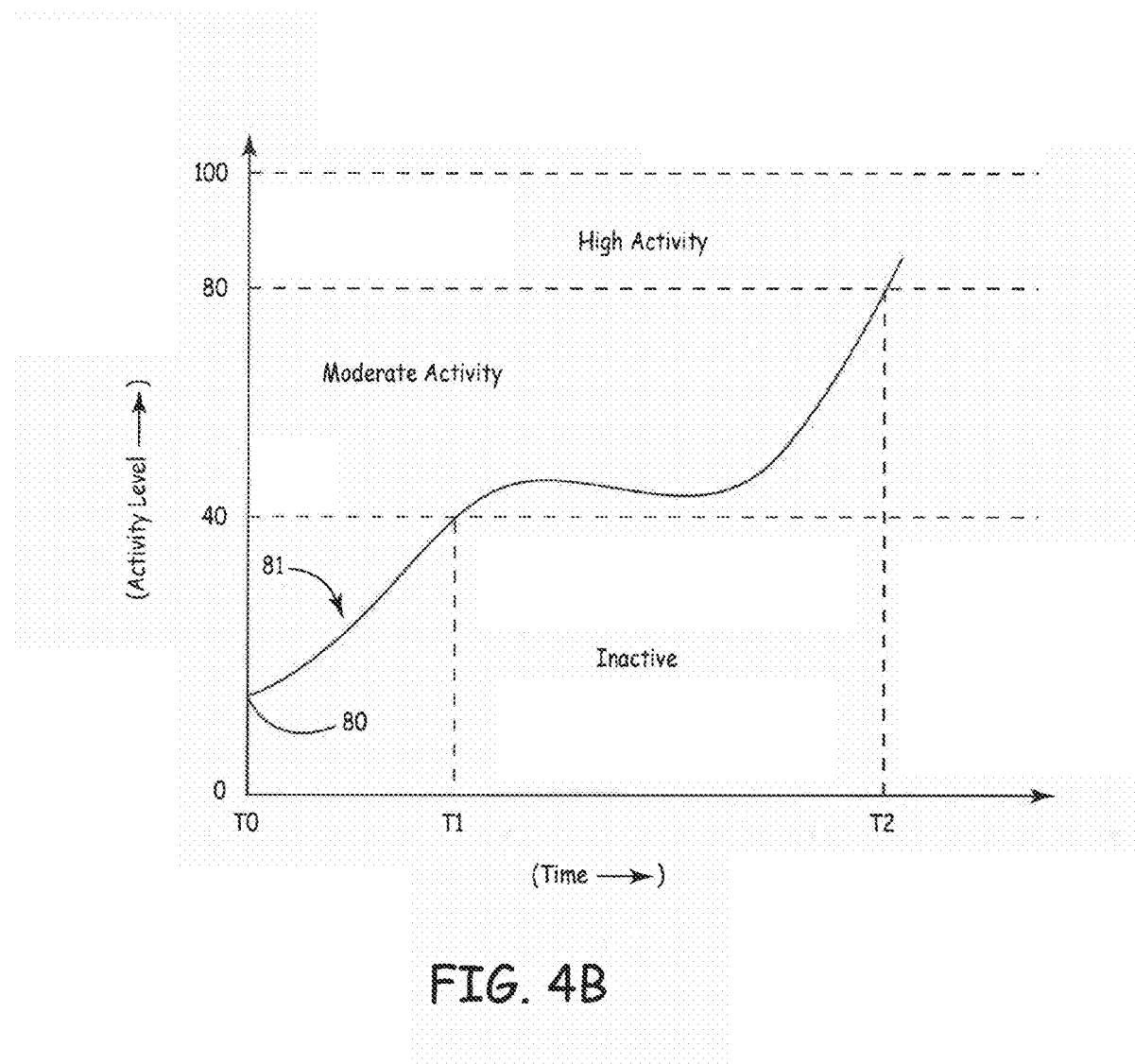
FIG. 4B is a conceptual graph illustrating defining and classifying activity states according to the current disclosure.

FIG. 4B is a conceptual graph of how signals from sensor 40 are used to classify a patient's activity state. According to this example, assume signals of sensor 40 may be processed to obtain an activity count that is indicative of an overall activity level of the patient. Specific processing steps used to obtain an activity count are largely beyond the scope of the current disclosure. More information associated with this processing is provided in commonly-assigned patent application entitled "Posture State Detection Using Selectable System Control Parameters", U.S. patent application Ser. No. 12/433,029, referenced above.

Next, assume for exemplary purposes that processing of the sensor signals yields an activity count that will range between 0 and 100, as shown along the Y axis of the graph. This activity level range may be referenced in activity state definitions, as by associating certain subsets of this range with defined activity states. For instance, an activity level of between 0-40 may be associated with an activity state definition of Inactive. Similarly, an activity level of between 40 and 80 may be associated with an activity state definition of Moderate Activity, and level between 80 and 100 may be associated with an activity state definition of High Activity. These may be stored as activity state definitions 52b (FIG. 3), for instance.

Activity state definitions 52b may be created using patient participation, as was described above in reference to creation of posture definitions 52a. For instance, a patient may be requested to undergo a specific activity, which may involve motion or lack thereof. While this activity is occurring, signals from sensor 40 may be obtained and processed in a predetermined manner. The resulting signal levels and/or associated signal level ranges may be stored in association with one of activity state definition 52b. The capture and storing of signals in this manner may be initiated by a user such as a clinician who is using programmer 20 (FIG. 1), for instance. In another example, activity state definitions may be pre-defined by a device manufacturer, or may be defined by a clinician or some other user without employing patient participation.

Once activity state definitions are created in any of the foregoing ways, the definitions may be used to classify a patient's activity state. For instance, as a patient goes about daily life, signals from sensor 40 may be obtained and compared to the signal levels stored within the activity state definitions. As a specific example, assume signals from sensor 40 are obtained and processed to provide an activity count of the type described above that describes a current activity of the patient. Assume further that in this example, the activity count detected from the patient is a value that lies within the range associated with the activity state definition of Inactive, as is the case for the activity signal 80 shown at time T0 in the diagram of FIG. 4B. Therefore, at this time, the patient will be classified as being in an activity state of Inactive. As a result of this classification, therapy that has been associated with this activity state may be delivered to the patient, and/or some other action may be initiated.

Next, assume the patient becomes more active such that the activity count trends upward towards 40. At time T1, the activity count obtained from the signals of sensor 40 crosses the boundary into the range associated with the definition for Moderate Activity. Therefore, the patient may at this time be classified as being in the activity state of Moderate Activity. As a result, a change in therapy may be initiated that corresponds with this increased activity level and/or some other action may be taken.

The patient's activity level may continue to trend upward, as shown in the example, until the patient's activity state is once again re-classified. This time, the patient is re-classified as being in the activity state of High Activity, as occurs at time T2. Again, some action may be initiated as a result of the reclassification. For instance, a therapy level (e.g., stimulation amplitude) may be increased to a level previously associated with the activity state of High Activity.

The example of FIG. 4B illustrates how an activity state that describes an overall patient activity level is used to classify the patient. Other types of activity state definitions may be created and used to classify the patient's posture state. For instance, some definitions may be defined that include a directional component, which may be expressed as one or more vectors. Such a vector may indicate a direction of acceleration, a direction of velocity, or some other direction associated with motion. As in the case described above, these one or more vectors may be stored in an activity state definition and thereafter compared to a vector obtained from a patient who is performing some activity. This comparison may be used to classify a patient's motion. For instance, a comparison of vectors may occur in a manner similar to that described above in reference to FIG. 4A, wherein a patient's posture is classified using posture definitions that include vectors.

As previously described, after a patient is classified in a particular activity state, some action may be taken in response to this classification. Some an action may include a therapy adjustment, issuance of a notification, the establishment of a communication session, the storing of data, or any other action. According with the current disclosure, the initiation of the action that is taken may be delayed based on a dwell time. That is, once the re-classification occurs, the patient must remain in this new activity state for the dwell time before the associated action is taken. If the patient exits this activity state before the dwell time elapses, the action will not be taken. This use of a dwell time introduces stability into the system, since temporarily assumed activity states do not result in the initiation of actions.

As was the case with dwell times associated with posture classifications, dwell times may be based on a most-recent stable activity state, the newly-assumed activity state, the transition between these two activity states, or some other condition. The dwell times may further be specific to a particular type of response. This is discussed further below.

As previously described, posture definitions and activity state definitions are each sub-classes, or sub-sets, of posture state definitions. A posture state definition may reference a posture, an activity state, or both. As an example, an Upright and Active posture state definition may be created that takes into account activity state (i.e., Active) and posture (i.e., Upright).

A posture state definition that takes into account both posture and activity state may be used in a manner similar to such definitions that take into account only one of posture and activity state. That is, signals from sensor 40 may be obtained and/or processed, and then compared to such posture state definitions to classify the patient's posture state. If the signals meet the requirements of the posture state definition, the patient may be classified in this posture state, and one or more actions may be taken in response to this classification. According to this disclosure, the initiation of such actions may be delayed based on a dwell time. In particular, a dwell time may be imposed between the time the re-classification occurs and the time the action is initiated. The action will not be initiated unless the patient does not exit the posture state for the duration of the dwell time.

Figure 5:
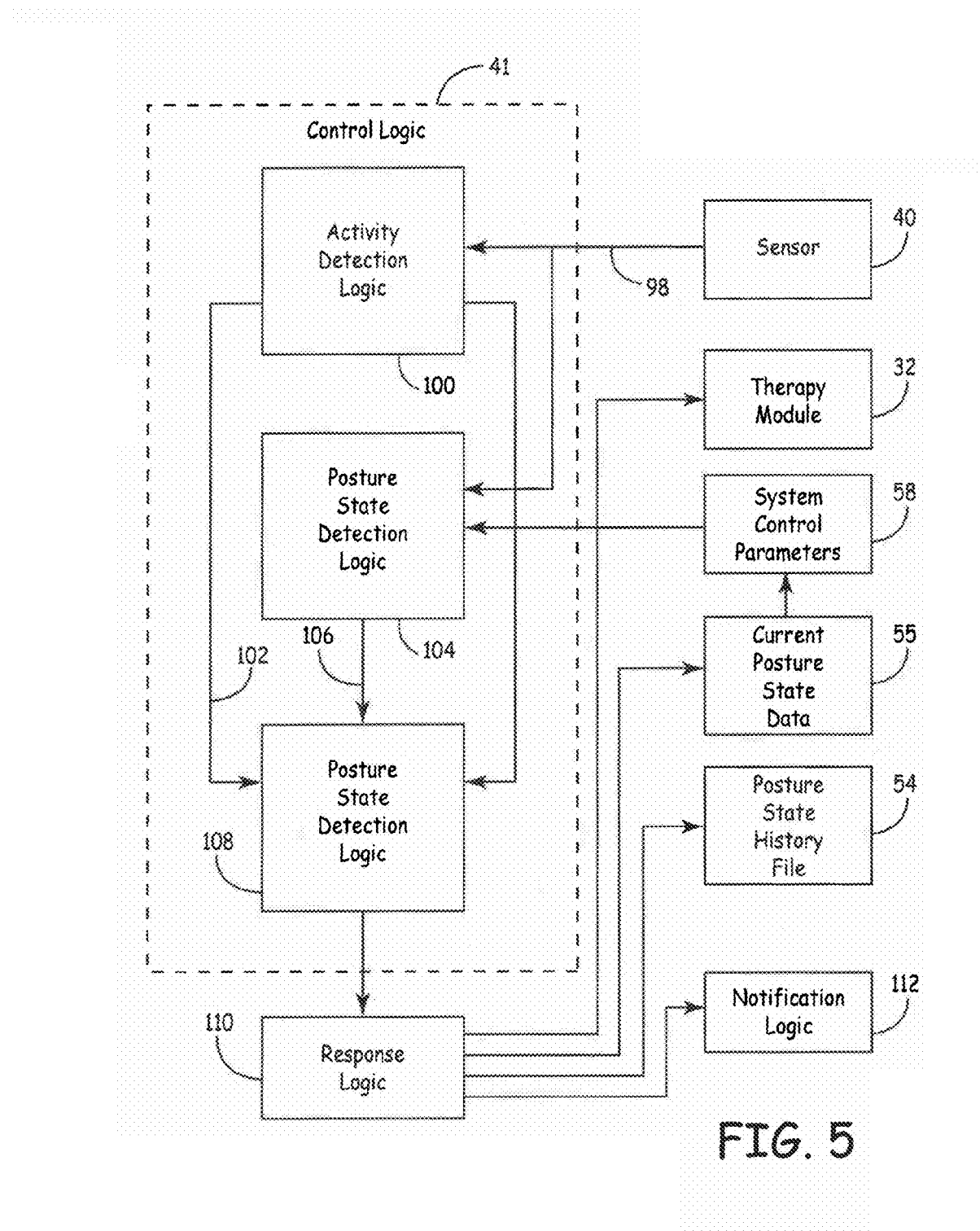
FIG. 5 is a functional block diagram illustrating processing sensor signals according to one embodiment of the disclosure.

FIG. 5 is a functional block diagram illustrating how signals from sensor 40 may be processed according to one embodiment of the disclosure. The signals from sensor 40 are provided to control logic 41 (shown dashed). This control logic embodies the functions that provide control for the system, and may be implemented in hardware, programmed instructions (as may be executed by processor 34 or another processor), or any combination therefore. This logic is shown to include various sub-functions, such as activity detection logic 100, posture detection logic 104, and posture state detection logic 108.

Signals from sensor 40 are provided to control logic 41 on interface 98. As previously discussed, for purposes of this description, sensor 40 is assumed to be a three-axis accelerometer that provides x-, y-, and z-axis signals. These signals are provided to activity detection logic 100 for use in deriving activity signals 102 that will be used to classify the patient's activity state. The way activity detection logic 100 processes signals of sensor 40 to generate the activity signals on interface 102 is largely beyond the scope of the current disclosure. One embodiment of such processing is provided in commonly-assigned patent application entitled "Posture State Detection Using Selectable System Control Parameters", U.S. patent application Ser. No. 12/433,029, referenced above.

In a like manner, signals from sensor 40 may be provided to posture detection logic 104 for deriving detected posture signals 106 that will be used to classify the patient's posture. For instance, a detected posture vector may be indicated on interface 106 for use in classifying a patient's posture in the manner described above. The way posture detection logic 104 processes signals of sensor 40 to generate the posture signals on interface 106 is largely beyond the scope of the current disclosure. One embodiment of such processing is provided in commonly-assigned patent application entitled "Posture State Detection Using Selectable System Control Parameters", U.S. application Ser. No. 12/433,029, referenced above.

The detected activity signals 102 generated by activity detection logic 100 and the detected posture vector signals 106 generated by posture detection logic 104 are provided to posture state detection logic 108 for use in classifying a patient's posture state. Posture state classification may be accomplished by comparing these obtained signals to posture state definitions 52 in a manner described above.

Posture state detection logic 108 may provide an indication of the patient's current posture state classification to response logic 110. This classification may be expressed as a binary or a master-bitted code that identifies the patient's posture state, which is based on at least one of the patient's posture classification and/or activity state classification.

As a result of the posture state classification received from posture state detection logic 108, response logic 110 may initiate one or more responses. For instance, response logic 110 may cause therapy module 32 to modify, begin, or stop the delivery of therapy. Response logic 110 may additionally or alternatively cause storing of data. For instance, response logic 110 may provide a signal to a storage device such as memory 36 to cause the updating of current posture state data 55 with the new posture state classification and/or to cause posture state history file 54 to be updated with to reflect the new posture state. Response logic may additionally or alternatively prompt notification logic 112 to generate a notification. As yet another example, response logic 110 may cause some type of communication session to be initiated, as via telemetry module 38.

In one embodiment, posture state detection logic 108 includes logic to impose a dwell time between the time a patient is classified in a posture state and the time some response is initiated as a result of the classification. This is discussed below.

The logic of FIG. 5 may be implemented in any combination of hardware (including discrete components, one or more processors, or any other type of circuitry), programmed instructions, or a combination of hardware and programmed instructions. Moreover, the manner in which the logic is partitioned in FIG. 5 is largely arbitrary, and is selected to aid in the discussion of the functionality. However, partitioning may occur in other ways. For instance, all of the logic of FIG. 5 may be combined into a single logic block. As another example, activity detection logic 100 and posture detection logic 104 may be combined. Many such combinations may be contemplated. Moreover, the interfaces between logic blocks may be implemented in many ways, and do not necessarily represent hardware interfaces. For instance, one or more of the logic blocks of FIG. 6 need not be physically connected to the logic blocks with which they share interfaces. Instead, such logic blocks may be logically connected, as by processor 34 transferring information between logical functions, or multiple software processes sharing information via shared locations in memory 36, for instance. Thus, the interfaces should be understood to represent flow of signals, control and/or data, and are not intended to limit the disclosure to any particular interconnect configuration. In sum, FIG. 5 should not be interpreted as limiting the disclosure to any specific implementation, interconnection, or partitioning of the logic, as many embodiments may be contemplated by those skilled in the art.

Figure 6:
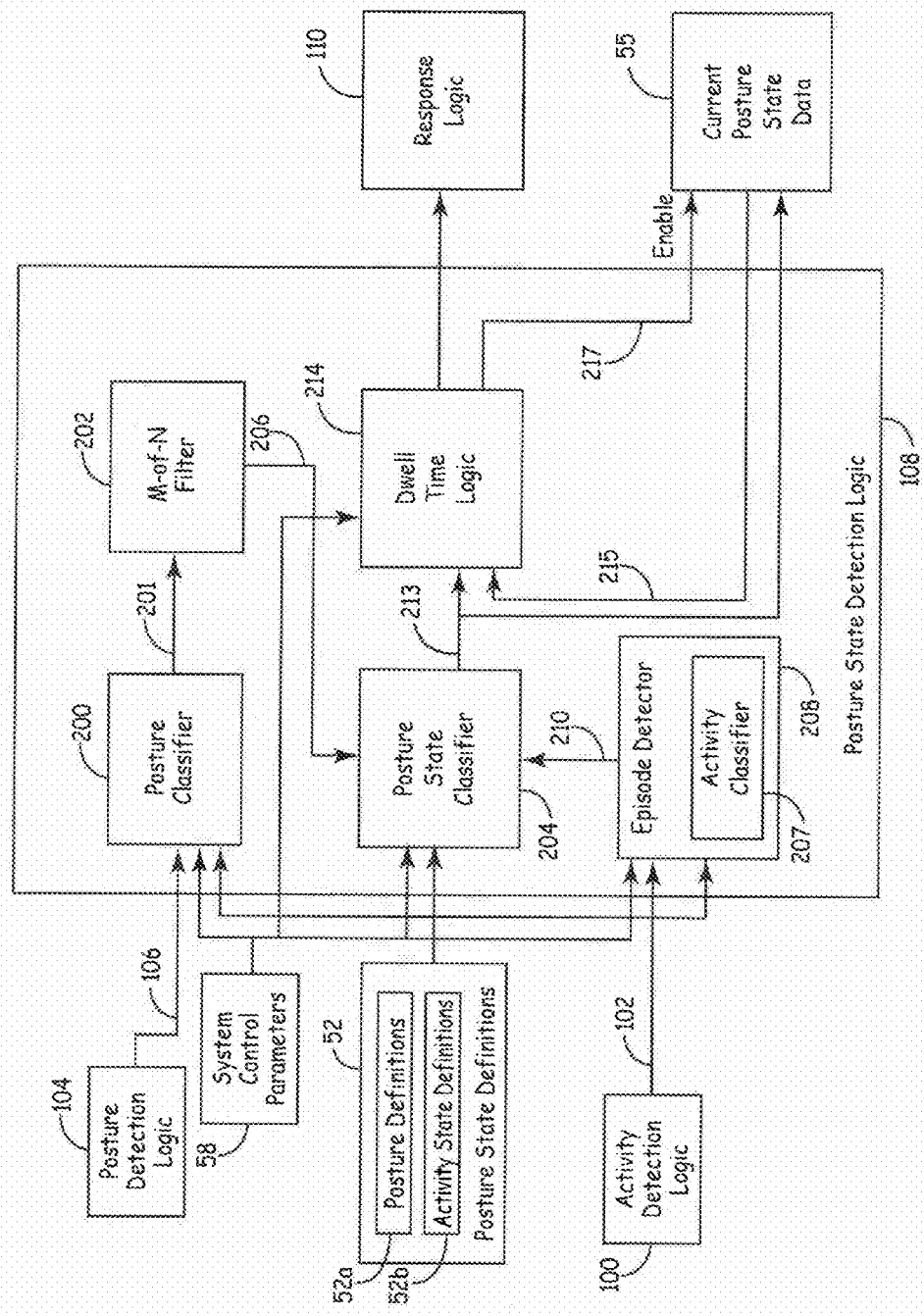
FIG. 6 is a functional block diagram of posture state detection logic.

FIG. 6 is a functional block diagram of posture state detection logic 108. Posture state detection logic 108 receives at least one activity signal on interface 102 from activity detection logic 100. For purposes of this discussion, it will be assumed this is a signal indicative of overall activity level, as was described above in reference to FIG. 4B. However, other one or more signals may be received from activity detection logic 100, such as signals indicating a vector providing a direction of velocity or acceleration, signals indicating activity in one or two specified directions, and so on.

Posture state detection logic 108 further receives one or more posture signals on interface 106 from posture detection logic 104. In one embodiment, this is a vector that is indicative of the patient's posture, as was described in reference to FIG. 4A. The patient's posture state is classified based on the received activity and/or posture signals, which are compared to the posture state definitions 52. In another embodiment, posture state detection logic 108 may receive only activity signals on interface 102 or only posture signals on interface 106 for use in classifying a patient's posture state, rather than both types of signals.

The posture signals received on interface 106 from posture detection logic 104 are provided to posture classifier 200. In the current example, these signals identify a detected posture vector $V_{pt}$ in three-dimensional space. Posture classifier 200 compares this detected posture vector to each of the posture definitions 52a, which are a sub-set of posture state definitions 52. Recall that in one embodiment, each such posture definition 52a may include a defined posture vector and an associated tolerance that specifies a relationship with the defined posture vector. Posture classifier 200 determines whether the detected posture vector on interface 106 has the relationship with any of the defined posture vectors that is specified by the corresponding tolerance for the defined postures. Many mechanisms are available for making this determination, which is largely beyond the scope of this disclosure. Examples of the mechanisms used to make a determination of whether the posture signals are associated with a defined posture are described in commonly-assigned patent applications entitled "Posture State Detection System and Method", U.S. Application No. 61/080,049 and Ser. No. 12/433,004, referenced above.

If the comparison between the signals (e.g., detected posture vector $V_{pt}$) on interface 106 and the posture definitions 52a results in a favorable comparison, an indication of the defined posture for this definition is provided by posture classifier 200. If no such match occurs, a code indicative of an Unclassified posture may instead by provided by the posture classifier 200 to indicate the detected posture vector is not associated with any of the posture definitions 52a. For instance, this may occur in the example of FIG. 4A if the detected posture vector $V_{pt}$ 71 is outside of both cones 64 and 70.

In one embodiment, the posture classification provided by posture classifier 200 is forwarded to M-of-N filter 202. M-of-N filter 202 determines whether M of the N most-recent posture classifications for the patient was a same classification. If so, an indication of this "M-of-N posture" is provided to posture state classifier 204 on interface 206. If M of the most recent N postures is not a same posture or has been indicated as being Unclassified, M-of-N filter 202 may, in one embodiment, continue to provide an indication of the M-of-N posture that was most recently detected by the M-of-N filter. In another embodiment, M-of-N filter may merely provide an indication that no M-of-N posture was detected. Use of the M-of-N filter is described further below.

As previously discussed, in addition to the posture signals received on interface 106, posture state detection logic 108 may additionally or alternatively receive one or more activity signals on interface 102. These signals may be forwarded to episode detector 208.

Episode detector 208 includes an activity classifier 207 that compares the received signals to each of the activity state definitions 52b to classify the patient's activity. This may be accomplished in the manner discussed above in reference to FIG. 4B, for instance. Episode detector 208 further determines whether the classified activity is indicative of an "episode" of activity. If so, an indication of an activity state for which an episode is detected is provided to posture state classifier 204 on interface 210. If, however, the signal on interface 102 does not reflect an episode of defined activity, an indication that no episode was detected is provided to posture state classifier 204. Use of episode detection is described further below.

In the foregoing manner, posture state classifier 204 may receive an M-of-N posture indication on interface 206 from M-of-N filter 202 and an indication of an activity episode on interface 210 from episode detector 208. In an alternative embodiment, only one of these indications may be provided to posture state classifier 204. Posture state classifier 204 then compares these indications to the posture state definitions 52. If one or more of the signals on interfaces 206 and 210 favorably compare to any of the definitions, an indication of the posture state is provided on interface 213. This indication may be an encoded value, a bit-mapped value, or some other type of indication of the patient's posture state.

As several examples, an indication of the Upright posture may be provided on interface 206, and an indication of the Active activity state episode may be provided on interface 210. This may favorably compare to an Upright & Active posture state definition, and thus an indication of the Upright and Active posture state may be provided on interface 213 to dwell time logic. Alternatively, an indication of the Upright posture may be provided on interface 206, and an indication that no activity episode was detected may be provided on interface 210. This may favorably compare to the Upright posture state which requires detection of the Upright posture without regard to the patient's activity state. Thus, an indication of the Upright posture state may be provided on interface 213. Conversely, an indication of an Active activity state may be provided on interface 210, resulting in an indication of an Active posture state on interface 213. This may be a posture state that requires only the Active activity state without regard to posture.

In some embodiments, and depending on the posture state definitions 52 that are in use within the system at a given time, the various signals received on interfaces 206 and 210 may result in the patient satisfying the requirements of multiple posture state definitions at once. In this case, in one embodiment, some hierarchical arrangement of the relative importance of these definitions may be used to determine which of these multiple posture states will be identified on interface 213 for use in generating a response. In another embodiment, different fields may be included in the posture state indication provided by posture state classifier 204 so that multiple posture states may potentially be identified simultaneously (e.g., one associated with just posture, another associated with just activity, and one associated with both).

The indication provided by posture state classifier 204 on interface 213 is forwarded to dwell time logic 214. Dwell time logic 214 may be used to ensure that once a patient is classified in a posture state, the patient will not exit that posture state for the predetermined dwell time. If the patient does exit the posture state before the dwell time elapses, no actions are taken in response to classification of the patient in this posture state. Only after this dwell time has elapsed will any actions be taken in response to the classification. In this manner, dwell times are utilized to ensure that transitory posture states that a patient may occupy for only a short period of time will not prompt actions such as an unwanted change in therapy. Moreover, the use of dwell times prevents a patient who is occupying a posture state that is at a boundary between two posture state definitions from triggering multiple actions (e.g., multiple therapy modifications) as the patient transitions between the two posture states over a short period of time. By selection of appropriate dwell times, an action in response to such short-term and repeated posture state re-classifications will be suppressed. An action (e.g., therapy change) will only be initiated after the patient finally settles in a stable manner into one or the other of the two posture states.

In one embodiment, dwell time logic 214 has access to current posture state data 55, which indicates the posture state in which the patient was most recently classified in a stable manner. Dwell time logic 214 compares this most recent stable posture state to the posture state which is indicated by posture state classifier 204 on interface 213. If a mismatch occurs, a potential re-classification of the patient's posture state may be underway. According to one embodiment of the current disclosure, before a response is initiated because of the posture state re-classification, a corresponding dwell time T is measured, as by a timer provided by dwell time logic 214. The posture state identified on interface 213 must remain stable throughout this dwell time T such that no other re-classification occurs. If this stability is maintained, dwell time logic 214 provides an indication to response logic 110 that posture state reclassification occurred and the appropriate one or more responses are to be initiated. As previously described, the appropriate responses may involve modification, cessation, or initiation of therapy delivery, storing of data, notification generation, an initiation or change in a communication session, and/or other responses involving system 10. On the other hand, if the dwell time does not expire before the signals on interface 213 again change, the dwell time is reset when the signal change on interface 213 is detected. The process may then be repeated. This will be described in reference to the figures below.

The dwell time that is being used by dwell time logic 214 may be "hard-coded" or may instead be programmable. This value may be programmed by a clinician, for instance, when IMD 12 is being initialized, and may be re-programmed any time thereafter as desired by the clinician.

In one embodiment, a dwell time may be automatically selected by the system based on current system conditions. For instance, the dwell time may be based, in full or in part, on current posture state data 55. This allows a different dwell time to be selected based on the patient's most-recently classified stable posture state as identified by current posture state data 55. As an example, a different dwell time may be selected if the patient's most-recently classified stable posture state reflects an Upright posture as compared to a posture associated with a reclining pose. As another example, if the patient was most-recently classified as being in an Active activity state, the dwell time may be different than if the patient's activity state was determined to be associated with inactivity. In yet another embodiment, the dwell time may be selected based on a most recent posture state transition. For instance, assume the patient's most-recent stable posture state, as indicated by current posture state data 55, is currently recorded as Upright & Active. Prior to this posture state, the patient was classified as being in a stable Upright & Inactive. This transition from Upright & Active to Upright & Inactive may be recorded by current posture state data 55 and used to select the dwell time. As yet another example, a newly-detected posture state indication provided on interface 213 may be used to select the dwell time, or the transition for the patient's most-recent stable posture state as indicated by current posture state data 55 to the newly-detected posture state indicated on interface 213 may be used to select the dwell time.

In one embodiment, the dwell time that is imposed by dwell time logic 214 may be response-specific. Thus, once a re-classification of posture state occurs on interface 213, a first dwell time may be imposed before a signal is provided to response logic 110 to prompt response logic 110 to initiate a first response (e.g., a change therapy delivery). A second dwell time that is different from the first dwell time may be imposed before dwell time logic 214 provides a signal to response logic 110 to initiate a second response (e.g., an event notification) and so on. If multiple such dwell times are being used, it is possible for the posture state classification appearing on interface 213 to remain stable long enough to prompt a first action associated with a first dwell time. However, the signals on interface 213 may change before a second, longer, dwell time elapses. Therefore, the second action that has been associated with this posture state classification is never initiated, since signal stability was not achieved for the second longer dwell time.

As may be appreciated, many embodiments are possible, including a simple approach that includes one dwell time that may be hard-coded, or a single dwell time that is programmable. In other embodiments, dwell times may be automatically selected based on monitored system conditions. In a more flexible system, different dwell times may be selected for different types of responses. According to this latter technique, the multiple dwell times may be hard-coded, programmable, automatically selected based on system conditions or some combination thereof.

In one embodiment, the posture state classification appearing on interface 213 will be used to update current posture data 55. In one embodiment, the time at which this occurs may be based on a dwell time. That is, any re-classification appearing on interface 213 will only be stored as current posture data 55 after an associated dwell time has elapsed, as indicated by dwell time logic 214 and represented by an enable signal on interface 217.

As may be appreciated, when dwell times are used, posture states classifications that appear on interface 213 for shorter than the corresponding dwell time will not prompt an associated response. Moreover, in an embodiment that utilizes dwell times to update current posture state data 55, posture states that are assumed for shorter than a corresponding dwell time will not be reflected by updating current posture state data 55 and/or may not result in updating of other records such as the posture state history file 54. Of course, if all posture state changes are to be used to update current posture state data 55 and/or posture state history file 54, this action need not be associated with a dwell time at all, or the dwell time may instead be set to 0. For instance, in one embodiment, it may be desirable to record all posture state classifications appearing on interface 213 for analysis purposes, regardless of how long these changes are maintained in a stable manner on this interface. Thus, there may be one or more logs that are maintained that do not have any dwell time imposed between a posture state re-classification on interface 213 and the recording of the posture state.

In one embodiment, dwell time logic 214 may utilize one or more software and/or hardware timers that are re-started each time current posture state signals on interface 213 are updated. The use of such timers in imposing dwell times is discussed below in reference to FIG. 10.

As described above, when response logic 110 receives an indication of timer expiration from dwell time logic 214, response logic 110 will initiate a corresponding response. This response may be a therapy modification that is controlled by processor 34 and/or delivered by therapy module 32. This response may alternatively or additionally be a notification controlled by notification logic 112, such as a communication delivered by telemetry logic 38 to an external device such as programmer 20, or may involve initiation of some other communication session. A response may involve updating current posture state data 55 and/or updating posture history file 54. Other responses are possible within the scope of the current disclosure.

It is appreciated that FIG. 6 is a functional block diagram. Any of the logic blocks shown in FIG. 6 may be implemented in hardware, programmed instructions, or some combination thereof. Moreover, the interfaces between logic blocks may be implemented in many ways, and do not necessarily represent hardware interfaces. For instance, one or more of the logic blocks of FIG. 6 need not be physically connected to the logic blocks with which they share interfaces. Instead, such logic blocks may be logically connected, as by processor 34 transferring information from one logic block to another, for instance, or by the logic blocks sharing through a common memory.

In some embodiments, all of the logic shown in FIGS. 5 and 6 may be included within a device (e.g., IMD 12) that is implanted within patient 14. In other embodiments, one or more of the logic blocks of FIGS. 5 and 6 reside outside of the patient's body. For instance, in one embodiment, the entire system of FIG. 6 may be implemented in a system that is worn outside the body of the patient. In another embodiment, sensor 40 and/or some portions of control logic 41 may be implanted within the patient and may communicate wirelessly with other portions of control logic 41 which are external to patient. Thus, many scenarios may be contemplated by those skilled in the art.

It may be appreciated that some logic blocks of FIG. 6 may be omitted or used for other purposes. For instance, episode detector 208 may be readily adapted for use in classifying a posture change episode, instead of, or in addition to, being employed to classify an activity episode. Similarly, M-of-N filter 202 may be adapted for use in classifying an activity state change, instead of, or in addition to, being employed to detect an M-of-N posture. Alternatively, one or both of the M-of-N filter 202 and episode detector 208 may be omitted entirely in some embodiments. This will be described further below in a more detailed description of this logic.

FIG. 7A is a timing diagram illustrating use of dwell times according to one exemplary embodiment of the disclosure. This diagram illustrates using detection of posture states to control delivery of therapy, although such detection may be used for initiating other responses, as discussed above. At time T0, it will be assumed that a first stable posture state has already been detected and is being used to control therapy delivery at a first therapy level, Therapy Level 1, which has been associated with posture state PS1. At time T1, a second, different posture state PS2 is detected. It will be assumed that a different therapy level, Therapy Level 2, has previously been associated with this posture state PS2. Rather than immediately change the therapy level to Therapy Level 2 in response to detection of posture state PS2, a dwell time is imposed. In particular, a timer/counter, which may be referred to as a "dwell timer", is started for a dwell time T1 that has been associated with this posture state change.

As previously discussed, many possibilities exist for selecting which dwell time will be used in a given situation. In a simple embodiment, one dwell time may be used for all posture state changes. In a more complex system, the dwell time may be selected on the particular posture state change that is occurring, on the most-recent stable posture state, on the newly-detected posture state, on a response type, and/or on some other monitored condition. For instance, the dwell time T1 may be selected based on the previous stable posture state PS1 that was assumed by the patient prior to the most recent posture state transition. Alternatively, the dwell time T1 may instead be selected based on the newly-detected posture PS2. In another embodiment, the specific transition from PS1 to PS2 may be used to select the dwell time. Other system conditions, such as physiological conditions of the patient (heart rate, blood pressure, etc.) may be used to select dwell time.

In the current example, dwell time DT1 expires at time T2, as indicated by arrow 220. Since the patient's posture state did not change throughout the dwell time, upon expiration of this dwell time, the level of therapy delivery is changed from Therapy Level 1, which is associated with PS1, to Therapy Level 2, which is associated with PS2. This change may occur as a step function, as shown by step function 224. However, in another embodiment, the change will occur over time, such as using a ramp or some other therapy adjustment function. Any type of linear or non-linear ramp or exponential attack function may be used, as shown by dashed lines 226, to achieve the target Therapy Level 2. The type of ramp or attack function used in the system and/or the time over which the change to the second therapy level occurs may be programmable. Moreover, the therapy adjustment time over which the adjustment occurs may likewise be programmable.

At time T3, the patient's posture state again reverts to posture state PS1. Rather than immediately revert back to Therapy Level 1, a dwell time is imposed. In this example, the dwell time selected for this situation, dwell time DT2, is different than the time DT1 used when the patient entered posture state PS2. This selected dwell time, which is represented by arrow 227, may be based on any of the considerations discussed above. Alternatively, a universal dwell time may be employed for use when any posture transition is detected, as previously mentioned.

As with the case discussed above, dwell time DT2 expires at time T4 without the patient shifting posture states. Therefore, the therapy level associated with PS1 is again delivered to the patient. This reversion to Therapy Level 1 is shown to occur as a step function 228. However, any type of linear ramp or decay function may be selected instead, as shown by dashed lines 230. The function selected to respond to a decrease in therapy level may be different than the function selected to respond to an increase in therapy level. That is, if desired, the one of functions 226 that is selected in response to a therapy increase is not required to correspond to the one of functions 230 that is selected in response to a therapy decrease.

In the foregoing manner, dwell times are imposed between the time a shift in posture state is detected and the time a response, which in this case is a therapy level adjustment, is initiated.

Figure 7B:
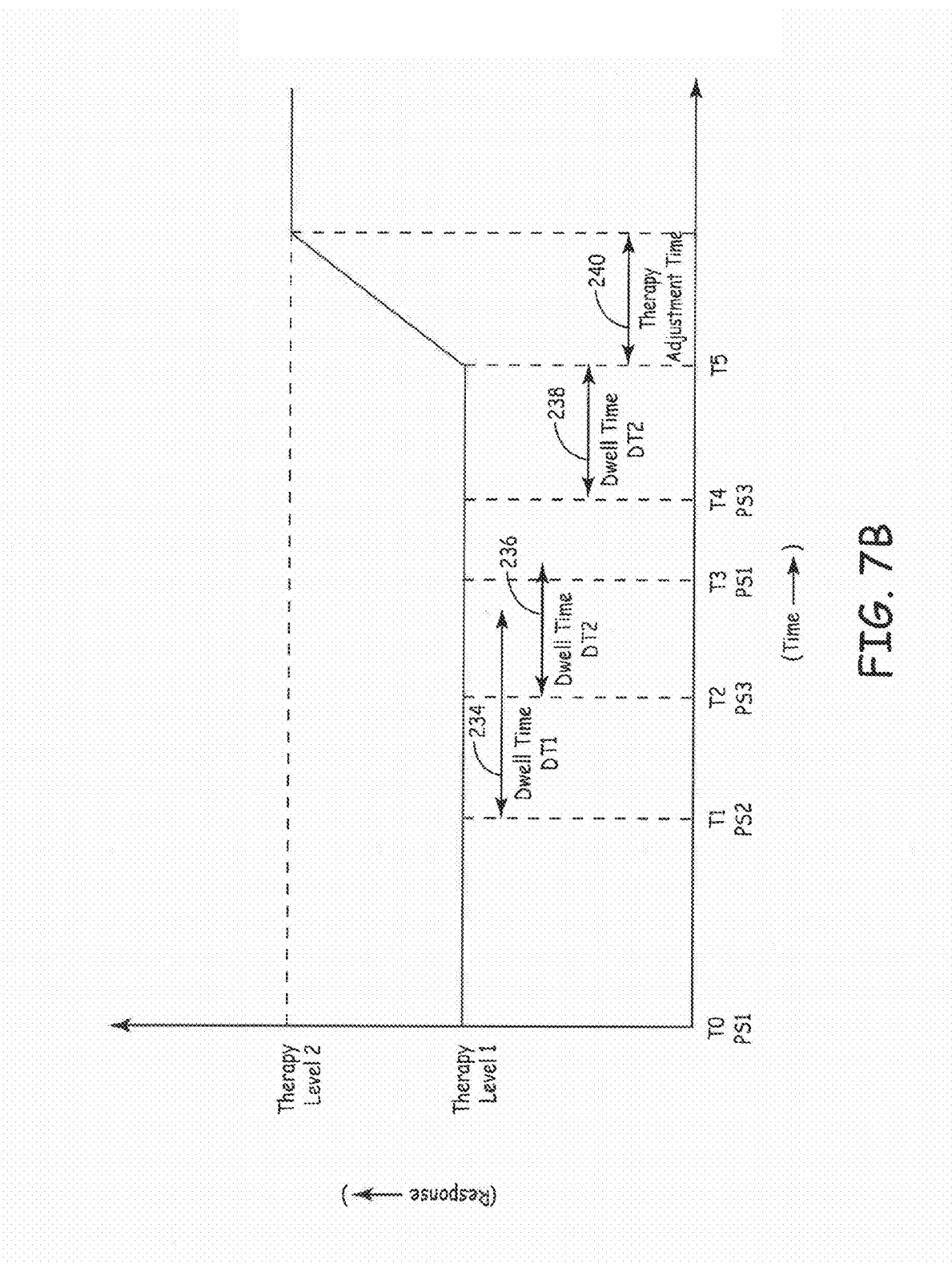
FIG. 7B is a timing diagram illustrating use of dwell times according to another exemplary embodiment of the disclosure.

FIG. 7B is a timing diagram illustrating use of dwell times according to another exemplary embodiment of the disclosure. This timing diagram, like the one discussed in regards to FIG. 7A, depicts delivery of therapy at various therapy levels. These therapy levels are delivered in response to detected posture states.

At time T0, a posture state PS1 has already been detected and is being used to deliver therapy at Therapy Level 1. At time T1, a second, different posture state PS2 is detected. As was the case in the foregoing example, a different Therapy Level 2 is associated with this posture state. Rather than immediately change the therapy level to Therapy Level 2 in response to detection of posture state PS2, a dwell time DT1 is imposed, as shown by arrow 234.

At time T2, before this dwell time DT1 expires, the patient's posture state changes again to a third posture state PS3, which is different from the original posture state PS1. Therefore, the timer associated with DT1 is reset, and a timer is started for this third posture state PS3, as indicated by arrow 236. The dwell time associated with this timer, DT2, is different from the dwell time DT1 used for PS2, although this need not be the case in other embodiments, as discussed above.

At time T3, the patient's posture again shifts back to the original posture PS1. Since this occurs prior to expiration of dwell time DT2, as may be seen by arrow 236, the dwell timer that was started upon the patient's classification in posture state PS3 is reset. Once again no therapy change occurs. Therapy is still being delivered at Therapy level 1, which is the therapy level associated with PS1. If no other action is associated with posture state PS1, in one embodiment, no dwell timer needs to be started. Therapy is already being delivered at the level associated with this newly-assumed posture state of PS1.

At time T4, the patient assumes posture state PS3 again. Therefore, a dwell timer is started to time dwell time DT2, as shown by arrow 238. At time T5, the dwell timer expires while the patient is still assuming posture state PS3. Therefore the associated response is initiated, which in this example, is a change in therapy to Therapy Level 2. As was the case in FIG. 7A, the change in therapy may be initiated as a step function. However, in one embodiment, the change occurs over time, as a ramp or some other therapy adjustment function, such as an exponential ramp function. The current example shows the change in therapy occurring as a ramp function, with the target Therapy Level 2 achieved over a therapy adjustment time indicated by arrow 240, which in one embodiment may be programmable.

The foregoing examples of FIGS. 7A and 7B assume that dwell times will be automatically selected based on the newly-assumed postures. For instance, in FIG. 7B, dwell time DT1 is used for newly-assumed posture state PS2, wherein dwell time DT2 is used for newly-assumed posture state PS3. In another embodiment, the previously-detected stable posture state could be used for this purpose. For instance, in FIG. 7B, a dwell time associated with posture state PS1 (rather than new posture state PS2) could be selected for use after the re-classification of the patient in posture state PS2 at time T1.

Figure 7C:
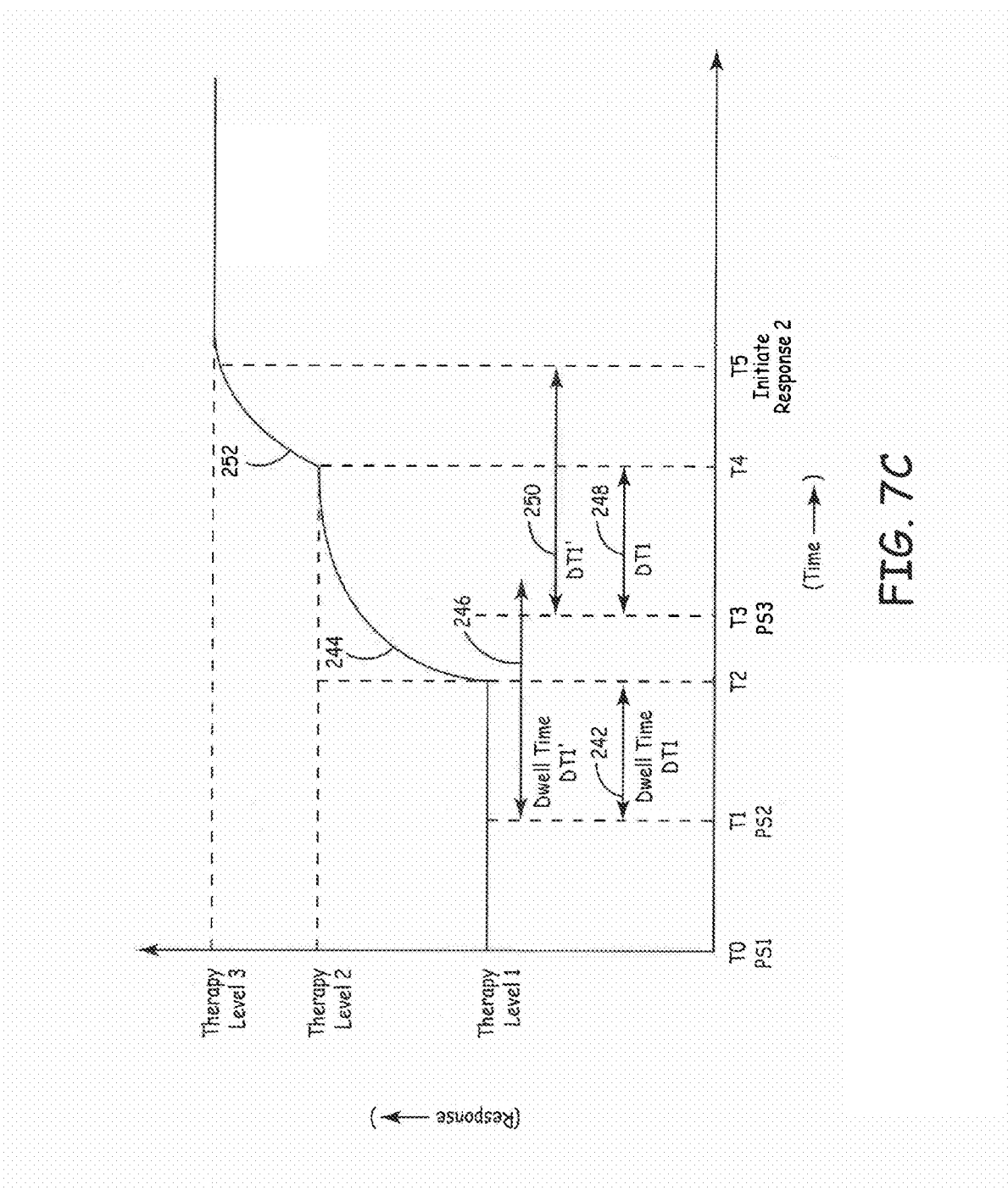
FIG. 7C is a timing diagram illustrating use of dwell times according to yet another exemplary embodiment of the disclosure.

FIG. 7C is a timing diagram illustrating use of dwell times according to yet another exemplary embodiment of the disclosure. This diagram describes use of multiple dwell times in response to a single detected posture state change. These dwell times are used to initiate multiple responses.

At time T0, it is assumed that a patient has been classified in a stable posture state PS1 and a therapy level associated with this posture state, Therapy Level 1, is being used to deliver therapy to the patient. At time T1, the patient is classified in a second, different posture state PS2. It will be assumed that a different Therapy Level 2 is associated with this posture state. Rather than immediately change the therapy level to Therapy Level 2 in response to re-classification of the patient's posture state, a dwell time DT1 is imposed. In particular, a timer is started for a dwell time DT1 that has been associated with this posture state change and that will be used to initiate a change in therapy level. This dwell time is represented by arrow 242. In addition, a second timer is started that is associated with a different dwell time DT1' that is longer than the dwell time DT1, as indicated by arrow 246. This second time will be used to initiate a response other than the change in therapy level. For instance, this other dwell time may be used to change the level of some therapy other than that represented by FIG. 7C, to start another therapy, stop another therapy, initiate a notification, prompt storing of data, start a communication session, or some other response.

At time T2, the first dwell timer associated with dwell time DT1 expires, as shown by arrow 242. Therefore, the therapy level is changed to Therapy Level 2. This change is not immediate in this example, but rather occurs according to an exponential attack function, as shown by curve 244.

At time T3, before the second dwell timer associated with dwell time DT1' expires, the patient changes his posture state to PS3. Thus, this second dwell timer is reset, and the response associated with this second timer is not initiated. Instead, at least one timer associated PS3 is started. In this example, a first dwell timer is started for a dwell time DT1, as shown by arrow 248. This dwell timer will be associated with a change in therapy to a level that is associated with PS3. A second dwell timer is also started in response to this change to posture state PS3 that will be used to initiate a second response. This second dwell timer will expire after the dwell time DT1', as indicated by arrow 250.

At time T4, the first dwell timer associated with time DT1 expires, and therapy levels are therefore changed to that associated with posture state PS3, which in this example will be assumed to be Therapy Level 3. As was the case with Therapy Level 2, the change does not occur immediately, but occurs using an exponential attack function shown by curve 252. At time T5, the second dwell timer associated with DT1' also expires, resulting in initiation of the second response, which may be any one of a number of responses associated with this shift to posture state 3.

In this example, the dwell times that are selected are the same for both posture changes. That is, when the posture change to PS2 occurs at time T1, the dwell time DT1 is selected for use in initiating a change in therapy level, and the dwell time DT1' is selected for use in initiating a second response. These same two dwell times are also selected for use when the shift to posture state PS3 occurs. Thus, this example shows that the dwell times may be response-specific, and not based on the posture states being assumed. Of course, the same dwell time may be used to initiate multiple responses in another embodiment. In still another embodiment, the selected dwell time may be both response-specific, and also based on posture state information (e.g., most-recent stable posture state, newly-assumed posture state, transition between the two, and so on).

It may be appreciated that FIGS. 7A-7C are merely exemplary, and many other scenarios may be contemplated for using one or more dwell times to control initiation of one or more responses as a result of one or more posture state changes.

FIG. 8 is an exemplary data structure that may be employed to associate posture states to responses. Column 260 lists the various posture states, PS1 through PSX. As previously discussed, these posture states may involve a posture, an activity state, or both. Example posture states may include Upright, Lying Down, Upright & Active, Active, and so on.

Each posture state may be associated with one or more responses, which are the responses initiated after the patient has been classified in that posture state. According to the current disclosure, the initiation of a response may be delayed by a corresponding dwell time.

Columns 262 of the data structure of FIG. 8 are associated with a first response, which involves a change to Therapy 1. In this example, these columns 262 list the therapy parameter values that are to be used to deliver the therapy. For instance, in row 264 for posture state PS1, the value for parameter 1 is listed as "PA", which may be a stimulation amplitude used to deliver electrical stimulation. Another parameter 2 has a value listed as "PF", which may be the frequency at which the stimulation is delivered. Yet another parameter N has a value listed as "PE", which may be the combination of electrodes used to deliver the stimulation. Any number of parameters may be included in columns 262, including a list of programs and/or program groups used to deliver therapy 1, a duty cycle of stimulation, stimulation pulse width, and so on.

In a similar manner, parameters may be selected for each of the other rows in the table for use in delivering Therapy 1 to a patient in response to the patient being classified in the corresponding posture state. If desired, for some posture states, it may be desirable to forego initiating any responses, keeping therapy delivery levels and other system operations as they were prior to detection of that posture state. This is indicated by not providing values for the various responses for posture state PSX in row 266, for instance. As yet another example, it may be desirable to halt delivery of a particular therapy, or start delivery of a new therapy, in response to detection of a particular posture state. Such information may likewise be contained in a data structure such as shown in FIG. 8.

Additional rows 268 and 270 are provided to list values for initiating one or more additional responses. For instance, rows 268 are associated with a second type of therapy that may be delivered to the patient. This therapy may, for instance, be associated with delivery of a therapeutic substance to the patient. Various parameter values may be provided to control this delivery in response to posture state classification. Yet other responses may include notifications that are delivered. Parameters that control such notifications may indicate how the notification is to be delivered, and so on.

In one embodiment, some posture states may be associated with no responses, and other posture states may be associated with one or more responses. Thus, in a most flexible embodiment, the types and/or numbers of responses to be generated as a result of each posture state may be selectable. If desired, the information contained in a data structure such as shown in FIG. 8 may be patient-specific, selected by a clinician at the time an IMD is initialized, and thereafter updated as deemed necessary.

To provide a system that requires fewer programming selections and is therefore more expedient to initialize, it may be desirable to "hard-code" the selection of responses that are available for a given posture state, and well as to pre-select at least some of the parameters associated one or more of the responses. This type of pre-selection process could be performed by a device manufacturer, for instance.

As previously discussed, in a streamlined environment, a single dwell time could be utilized to initiate all responses. This same dwell time could be selected regardless of the patient's previous or current posture state. According to a more flexible approach, a dwell time could be selected based on response, as shown in FIG. 7C, and/or based on posture state data, as illustrated in FIGS. 7A and 7B.

FIG. 9 is an exemplary data structure that may be employed to select dwell times according to one embodiment. Column 280 lists posture state information. Rows 282 are associated with the most-recent stable posture state (i.e., "current" posture state), rows 284 are associated with the posture state that is newly detected, and rows 286 are associated with a posture state transition.

According to these embodiments, if desired, dwell times may be selected based on the most-recent posture state, as will be reflected by the current posture state data 55, in one implementation. Alternatively, dwell times may be selected based on the newly-assumed posture state, as will be provided on interface 213 to dwell time logic 214 of FIG. 6. In yet another embodiment, the specific transition between the current and the new posture state may be used to select the dwell time. Thus, a system may choose to operate according to the selections provided by rows 282, by rows 284, or by rows 286 in one embodiment. According to a more streamlined approach, the system need not take into account posture states when selecting dwell times.

According to another aspect, the dwell times may be selected in a manner that is response-specific. This is shown in reference to columns 288. One or more types of responses may each include a respective dwell time. In the example shown, each of the posture states shown in rows 282 is associated with a different dwell time for each type of response (e.g., Therapy 1 modification, Therapy 2 modification, etc.). According to a more streamlined approach, a same dwell time may be used for all types of responses.

In another embodiment, the dwell times may be specific to how a response will be initiated, as is shown in regards to columns 290. For instance, if the new posture state will ultimately result in a therapy level increase (e.g., increase in stimulation amplitude), a first dwell time may be selected. Conversely, if the change to the new posture state will result in a therapy level decrease, a different dwell time may be selected. According to this approach, it may be desirable to use longer dwell times when an increase in amplitude will be delivered as a result of the posture state change, since this will provide more assurance that the patient is indeed remaining in this posture state prior to the time delivery of the increased therapy is initiated.

As another example, one dwell time may be selected if therapy is to be initiated as a result of a posture state change, and yet another, different dwell time may be selected if the posture state change will result in cessation of a therapy. In this manner, dwell times may be selected based on the type of change in a response, rather than in the type of response itself.

In another embodiment, some other measured condition may be used to select dwell times, such as a physiologic condition that may be determined using sensors. Examples include heart rate, blood oxygen levels, blood pressure, and so on. Many such conditions may be contemplated by those skilled in the art. This is as exemplified by columns 292.

The selection as to which method to use to select dwell times may, in one embodiment, be programmable. For instance, a clinician may decide to use dwell times selected from the intersection of rows 282 and columns 288. Alternatively, a clinician may decide to utilize those selected from the intersection of rows 284 and columns 290. Many combinations are possible.

As previously discussed, selection of dwell times may be greatly simplified through the use of a single dwell time that is applied to initiation of all responses, and which is used regardless of the posture state change that is occurring.

Figure 10:
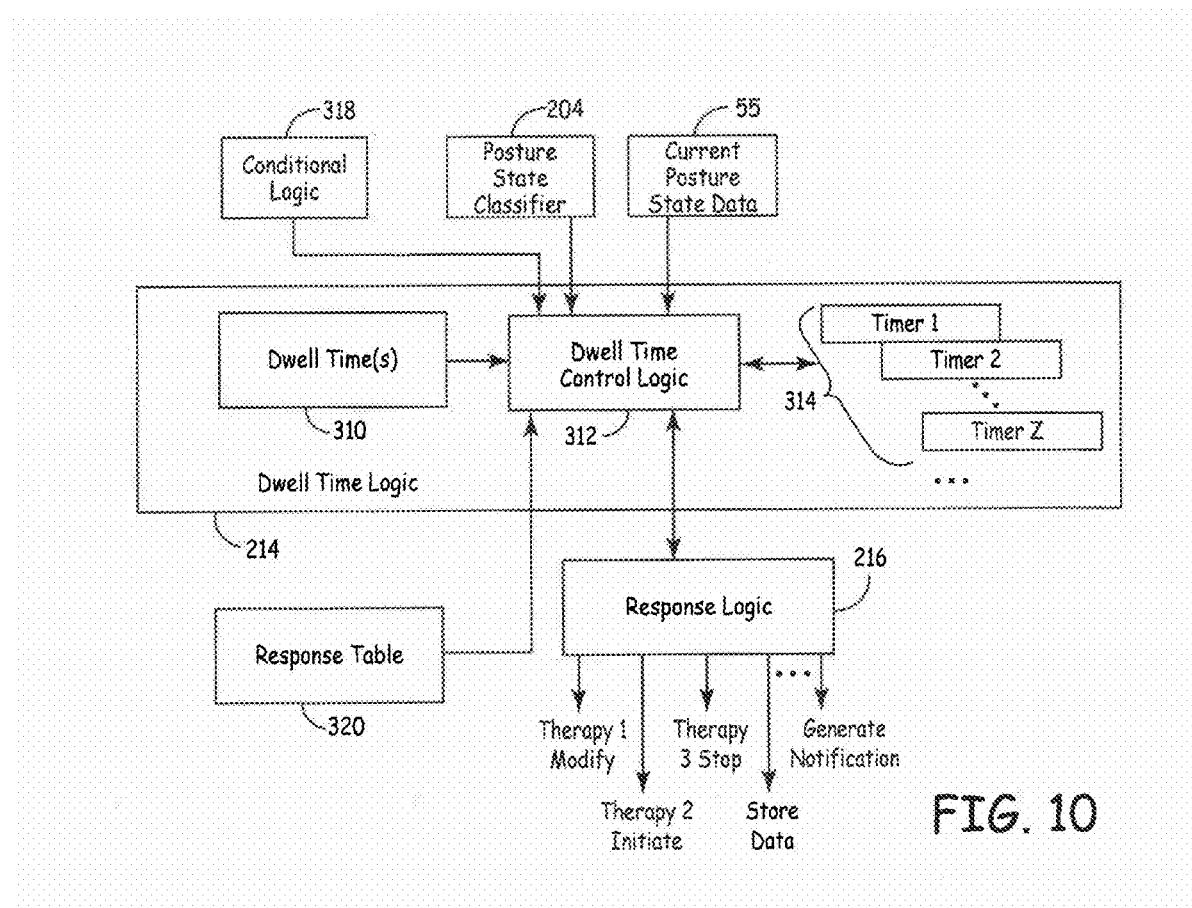
FIG. 10 is a functional block diagram of one embodiment of dwell time logic.

FIG. 10 is a functional block diagram of one embodiment of dwell time logic 214. The one or more dwell times that are in use in the system are represented by dwell time(s) 310. In one embodiment, the dwell times are programmable, and the selected values may be stored in a data structure such as shown in FIG. 9, or any other one or more data structures, the formatting of which is largely unimportant. Such a data structure may be retained in a storage device such as memory 36, for instance, or may be retained within a storage device of an external device such as programmer 20. In the latter case, some or all of the dwell times may be provided from an external device such as programmer 20 during initialization of the device, or as needed. Alternatively, some or all of the data may be selected by a device manufacturer for inclusion in IMD 12, as by providing this information in a ROM, for instance.

The dwell time(s) are accessible to dwell time control logic 312. Also accessible to dwell time control logic 312 is the output of the posture state classifier 204, as well as the current posture state data 55. When a change in posture state detected, as may be accomplished by determining that the posture state classification from posture state classifier 204 is different from the posture state indicated by current posture state data 55, dwell time control logic 312 controls how this posture state change will affect operation of one or more timers 314. In particular, if one of the timers 314 is measuring a dwell time at the time a posture state change is detected, this timer is reset and the corresponding response will not be initiated. This is because the full dwell time did not elapse prior to another change in posture state, as described in reference to FIGS. 7A-7C.

Additionally, dwell time control logic 312 may load one of timers 314 with an appropriate dwell time and start that timer. The dwell time to use may be selected based on the current posture state data 55, which indicates the stable posture state in which the patient was classified just prior to the most recent classification. This corresponds with rows 282 of FIG. 9, for instance. Alternatively, the dwell time may be selected based on the output of the posture state classifier 204, which indicates the newly-assumed posture state classification. This corresponds with exemplary rows 284 of FIG. 9. Alternatively, the transition between the two posture states may be used to select the dwell time, as illustrated by exemplary rows 286 of FIG. 9.

Dwell time control logic 312 may also receive an indication from conditional logic 318, which may indicate physiologic and other conditions associated with the system on which the dwell time selection may be based. All of the received inputs may be used by dwell time control logic 312 to select one or more appropriate dwell time(s) 310 that corresponds to the current situation. Each of the selected dwell times may be loaded into a corresponding one of timers 314 and the timer may be started. This may involve starting a single timer, or multiple timers, as discussed in relation to FIG. 7C.

For each timer, dwell time control logic 312 may track the one or more responses which are to be initiated as a result of timer expiration. Such information may be obtained from a response table 320, which may be similar to that shown in FIG. 8. The formatting and content of this data structure is largely irrelevant. What is important to note is that dwell time control logic 312 associates a timer with one or more responses. Upon expiration of a timer, dwell time control logic 312 is thereby able to provide a signal to response logic 216 to indicate a type of response that is to be initiated. As described above, such a response may involve one or more of modification of a therapy, initiation of a therapy, cessation of a therapy, the storing of data, initiation of a communication session, initiation of a notification, and so on. If desired, such a response may even involve the timing associated with updating current posture state data 55 to reflect the new posture state indicated by posture state classifier 204. Any type of response that may be usefully employed in the system may thereby be associated with a dwell time in this manner.

FIG. 10 shows the use of multiple timers. If multiple dwell times are to be used in a single-timer environment, dwell time increments may be employed. For instance, if two responses are to be associated with a posture state change, and those responses are to be initiated at a first time T1 and a longer time T2, respectively, the first time T1 may be loaded into the dwell timer. Upon expiration of this time T1, a time increment of T2–T1 may be loaded in the same timer. This incremental time may then be used to initiate the second response.

The logic of FIG. 10 may be implemented in any combination of hardware (including discrete components, one or more processors, or any other type of circuitry), programmed instructions, or any combination thereof. For instance, dwell time control logic 312 may include one or more processors executing programmed instructions. The one or more timers may be software timers, hardware timers, or some combination thereof. Moreover, the manner in which the logic is partitioned in FIG. 10 is largely arbitrary, and is selected to aid in the discussion of the functionality. However, partitioning may occur in other ways. Additionally, the interfaces between logic blocks may be implemented in many ways, and do not necessarily represent hardware interfaces. For instance, one or more of the logic blocks of FIG. 10 need not be physically connected to the logic blocks with which they share interfaces. Instead, such logic blocks may be logically connected, as by processor 34 transferring information from one logic block to another, for instance. Thus, the interfaces represent flow of signals, control and/or data, and are not intended to limit the disclosure to any particular interconnect configuration. In sum, FIG. 10 should not be interpreted as limiting the disclosure to any specific implementation, interconnection, or partitioning of the logic, as many embodiments may be contemplated by those skilled in the art.

Figure 11A:
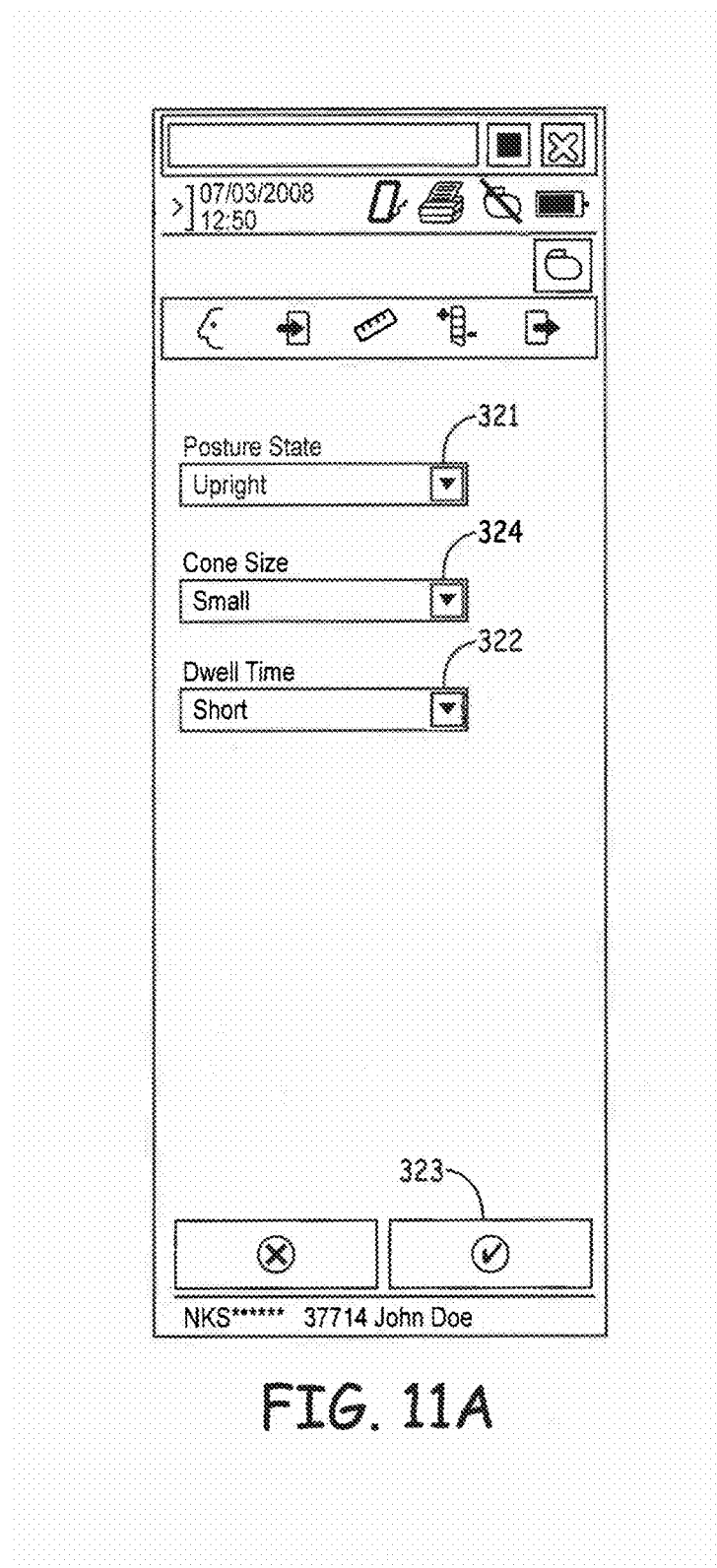
FIG. 11 is an example user interface screen that may be employed to select dwell times according to one embodiment.
FIG. 11B is another example user interface screen that may be employed to select dwell times according to another embodiment.

FIG. 11A is an example user interface screen that may be employed to select dwell times according to one embodiment. This type of interface may be provided by a clinician programmer or some other programming device. Many of the icons appearing on this menu are beyond the scope of the current disclosure, and therefore will not be discussed. Of importance is drop-down menu 321, which is used to select from a list of defined posture states. In one embodiment, this list may be populated by a device manufacturer. In another embodiment, this list may be populated, at least in part, as a user, such as clinician, defines posture states for use in treating a particular patient. Thus, in one embodiment, this list may be at least partially patient-specific.

Once a posture state (e.g., Upright) has been selected, a dwell time may be selected for association with this posture state using a second drop-down menu 322. This menu may display a list of dwell times described in absolute terms (e.g., seconds, minutes or some other unit of measure), or may instead display a list of dwell times described in relative terms (e.g., short, medium, long). These relative descriptors may be defined by a user, such as a clinician, or "hard-coded", as by the device manufacturer. Once this selection and association is made, a save function may be invoked, as by selecting button 323. This will make the association between the selected posture state and the dwell time. Such an association may be stored in a data structure such as that shown in FIG. 9, for instance.

In one embodiment, the posture state that is selected in the foregoing manner is that posture state to which the patient is transitioning. That is, dwell times are associated with the newly-assumed posture states, as shown in rows 284 of FIG. 9, and as illustrated by FIGS. 7A and 7B. In another embodiment, the selected posture state may be associated with the posture state reflected by current posture state data 55, if desired.

The user interface screen of FIG. 11A includes a third drop-down menu 324 for use in selecting cone size. This relates to the size of cone used to define a posture, as is shown in reference to FIG. 4A. This is largely irrelevant to the current disclosure, and will not be described further.

As may be appreciated, the user interface shown in FIG. 11A supports a streamlined system that does not provide for selection of dwell times that are based on a posture state transition, a response type, a change in response, or to any other conditions. In a more complex system, additional drop-down menus may be used to add more complexity to the selection of dwell times. This is exemplified with respect to FIG. 11B.

Figure 11B:
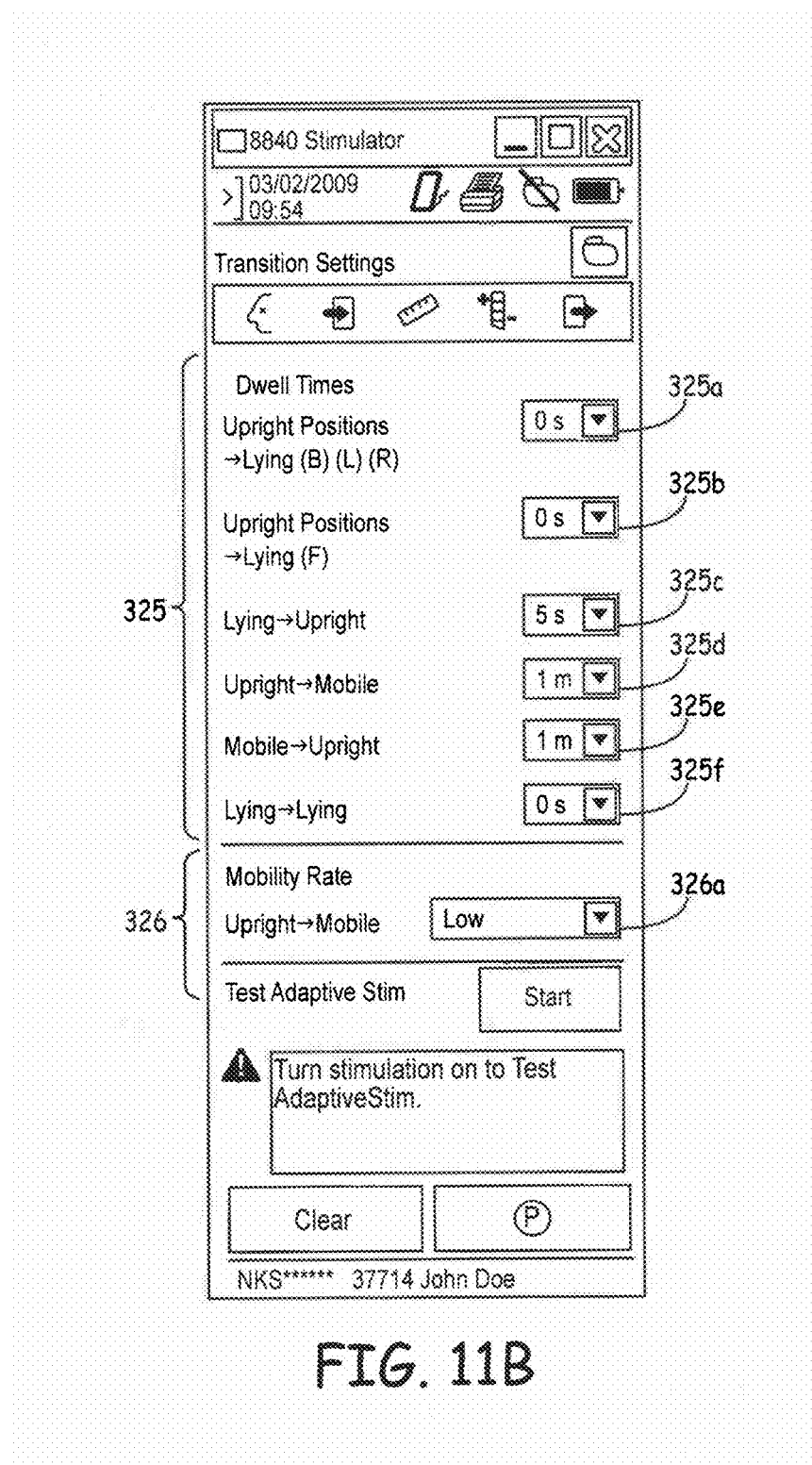

FIG. 11B is another example of a user interface according to one aspect of the disclosure. As was the case with FIG. 11B, this interface may be provided by a clinician programmer or some other programming device. In this example, dwell times are selected based on posture state transitions rather than based on the potentially new posture state, as was described in reference to FIG. 11A. Such dwell times that are based on posture state transitions were described in reference to rows 286 of the data structure shown in FIG. 9, for example.

According to the example screen display, screen portion 325 is employed by a user to select a respective dwell time for each of six types of posture state transitions. In particular, drop down menu 325a selects a dwell time that corresponds to a transition from an Upright posture state to any one of three lying down postures. These three lying down postures includes the patient lying on his/her Back (B), lying on the Left Side (L) and lying on the Right Side (R). Thus, in this embodiment, the same dwell time will be used whenever any of these three posture state transitions occur.

In a similar manner, drop down menu 325b selects a dwell time that corresponds to a transition from the Upright posture state to a posture state of lying on the patient's Front (F), or face down. Drop down menu 325c selects a dwell time for use when transitioning from any Lying down posture state (including Front, Back, Right Side, and Left Side) to an Upright posture state.

Drop down menu 325d is used to choose a dwell time that will be employed when a transition from an Upright posture state to a Mobile posture state is detected. According to one example, the Upright posture state may be defined in terms of an Upright posture and a relatively low activity level, whereas the Mobile posture state may be expressed in terms of an Upright posture and an activity level above some selected "Mobile" threshold level. Thus, in this example, the dwell time selected via menu 325d will be used whenever a patient that is standing upright begins an activity that causes the detected activity level to transition above the threshold associated with the Mobile posture state. Yet another drop down menu 325e may be used to select a dwell time for the opposite transition involving shifting from the Mobile posture state to the more sedentary Upright posture state.

Finally, drop-down menu 325f is used to select a dwell time that will be employed whenever the patient transitions from one lying down posture state (e.g., Back, Front, Left Side, Right Side) to a different lying down posture state.

In screen portion 325, any of the times may be selected in seconds (s) or minutes (m). Additional and/or alternative time units may be used in other embodiments.

In screen portion 326, the threshold used to define the posture state of Mobile is selected. In particular, drop down menu 326a allows a user to select the Mobile threshold level that will determine when a patient transitions between a relatively sedentary Upright posture state to the more active Mobile posture state. This example shows the value of "Low" being selected as this threshold. It will be appreciated that other values may be defined to populate menu 326a, such as "Moderate", "High", and so on.

In this example, the value selected for this threshold level (e.g. "Low") is a relative, rather than an absolute, value. Typically, this relative threshold level will be associated with some absolute value obtained from processing signals of sensor 40. For instance, this value of "Low" may be associated with a signal value (e.g., "40") obtained from processing signals of sensor 40, as is described above in reference to FIG. 4B. This association could be "hardcoded" by the device manufacturer. Alternatively, this association may be created by an end user such as a clinician using another screen display of the user interface. In yet another embodiment, absolute threshold values may be used to directly populate the drop down menu 326a.

As may be appreciated, the number of posture states that are available for definition and use within the system is virtually limitless. Thus, the various combinations of posture states that may be used in a user interface of the type shown in FIGS. 11A and 11B are also virtually limitless. These combinations may be predefined by a device manufacturer in one embodiment. In another embodiment, the types of transitions and threshold values that are available in screen portions 325 and 326 may be selectable, at least in part, by the user. For instance, as the user defines various posture states, the user may also be allowed to determine how the posture states are grouped and displayed for dwell time selection purposes. Thus, the dwell time screen displays such as those shown in FIGS. 11A and 11B may be generated dynamically using posture state definition and dwell time selection data provided by a user such as a clinician. This latter approach provides a high degree of flexibility, allowing the user to determine the degree of specificity with which dwell time logic will operate.

Figure 12:
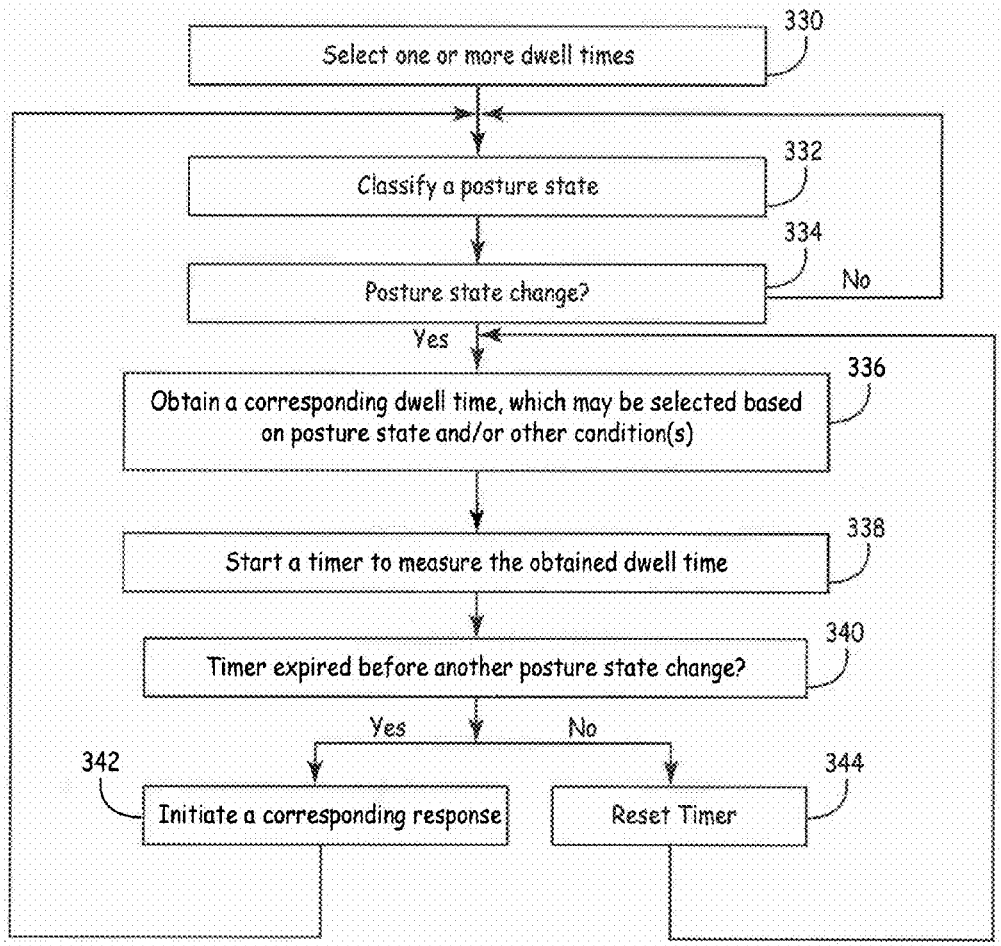
FIG. 12 is a flow diagram according to one embodiment of the current disclosure.

FIG. 12 is a flow diagram according to one embodiment of the current disclosure. This process may be executed, for instance, by dwell time logic 214 of FIGS. 6 and 10. One or more dwell times are selected for use within the system (330), as may be accomplished via a user interface such as that shown in FIG. 11A. A posture state may then be classified as the patient goes about daily life (332). If this posture state classification does not indicate a change in the patient's posture state (334), execution returns to step 332 for re-classification of the patient's posture state. Otherwise, processing continues to step 336, where a corresponding dwell time is obtained. This dwell time may be selected based on posture state data and/or other conditions. These other conditions may include the types of response(s) that are to be initiated, the types of changes in response that may occur, or other conditions such as physiological conditions.

The selected dwell time is used to start a timer (338). If the timer expires before another posture state change occurs (340), a corresponding response is initiated (342). Processing then returns to step 332 and the method is repeated. Otherwise, if in step 340 the timer does not expire before another posture state change is detected, the timer is reset (344) and processing returns to step 332 to repeat the method.

As may be appreciated, according to another embodiment, more than one dwell time may be selected in step 336, potentially resulting in the use of multiple timers in step 338, and the possible initiation of multiple responses in step 342. Many alternative embodiments will be apparent to those skilled in the art, including embodiments that may re-arrange the ordering of the method steps.

The foregoing discussion focuses on the use of dwell times to impose a delay between the time a posture state is detected and the time a response is initiated based on the detected posture state. An alternative or additional mechanism that may be used for this purpose involves episode detection. Episode detection may be performed to detect an episode of activity, an episode of posture, or an episode related to a change in posture state. In the exemplary system shown in FIG. 6, the episode detection is shown being performed in relation to an activity state. Therefore, for the following discussion, this embodiment will be assumed. However it will be understood that episode detection is not limited to this purpose.

Episode detection may be appreciated by returning to the diagram of FIG. 4B. In that example associated with that diagram, signals from sensor 40 may be processed to obtain an activity level that may range from 0 to 100. Activity state definitions are created that reference this possible range of signal values. As an example, an activity state of Inactive may be defined that is associated with range 0-40. Another activity state of Moderate Activity may be defined for the range 40-80. Yet a third activity state called High Activity may be defined for the range from 80-100.

Next, these activity state definitions may be used to classify a patient's activity state. In particular, signals from sensor 40 may be processed to obtain a current level of activity. This activity level over time is shown as signal 81 in FIG. 4B. At time T0, this signal lies in the Inactive range. Without use of episode detection, this signal will be re-classified as being in the Moderate Activity range after it crosses the activity level of 40. Another re-classification occurs as this signal trends upward to cross the boundary of 80 into the High activity range.

Episode detection changes the point and time at which this re-classification occurs. Instead of the detected signal level being compared directly to boundary values reflected by the posture state definitions (e.g., boundaries of 40, 80, and so on), the boundary values used to detect a posture state transition are adjusted using transition thresholds. Moreover, time requirements called transition durations are imposed, requiring the posture state transition to be maintained above/below the adjusted boundary for a selected period of time before the posture state re-classification is recognized. This may be described in reference to FIG. 13.

Figure 13:
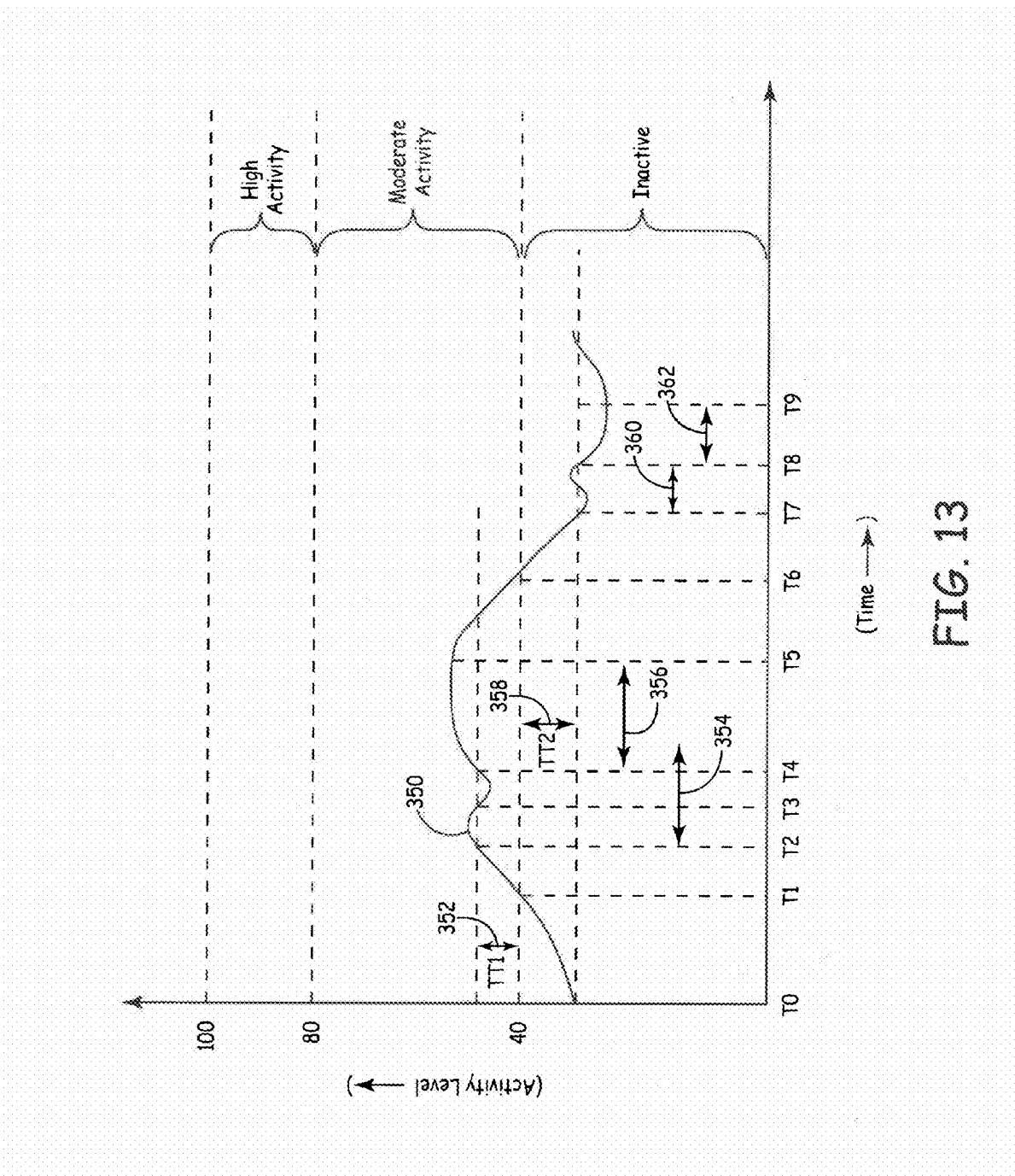
FIG. 13 is a timing diagram illustrating use of episode detection according to one embodiment of the disclosure.

FIG. 13 is a timing diagram illustrating use of episode detection according to one embodiment of the disclosure. Signal 350 is a representation of an activity level derived by processing signals of sensor 40 to obtain an indication of activity level of the patient. The activity state definitions that are discussed above in reference to FIG. 4B will be assumed to be in use in this example, as shown by the y-axis of FIG. 14. At time T0, the patient's activity state will be classified as Inactive. At time T1, the patient's activity state would be re-classified to Moderately Activity if episode detection were not in use in the system. However because episode detection is being used, the value of "40" is not used as the re-classification boundary between the activity states of Inactive and Moderate Activity. Instead, this boundary is adjusted by an amount determined by a selected transition threshold of TT1, represented by arrow 352. In particular, re-classification will occur at 40+TT1, where TT1 is a selected transition threshold value. For instance, this value may be selected as "5" such that the re-classification will not occur until the activity level that is indicated by signal 350 reaches 40+5, or 45.

Because of use of transition threshold TT1 to adjust the boundary, as represented by arrow 352, re-classification of the patient's activity level will not potentially occur until time T2, at which time signal 350 exceeds the level for 40+TT1. When the signal level exceeds this threshold of 40+TT1 at time T2, a second aspect of episode detection becomes apparent. At this time, a timer is started that is associated with a transition duration. This timer is represented by arrow 354 in FIG. 13. Signal 350 must remain above the threshold of 40+TT1 for the entire transition duration for an episode of activity to be detected.

In the current example, signal 350 dips below threshold 40+TT1 at time T3, before expiration of the transition duration represented by arrow 354. As a result, the timer for the transition duration is reset, and no episode is detected for an activity state of Moderate Activity.

Next, at time T4, signal 350 once again crosses the threshold of 40+TT1. The timer associated with this threshold crossing is again re-started to time an applicable transition duration, as indicated by arrow 356. This time, signal 350 does remain about the threshold of 40+TT1 until after time T5 when the timer expires, as indicated by arrow 356. Therefore, at time T5, an episode of activity will be reported with respect to the activity state of Moderate Activity.

Signal 350 eventually trends downward, crossing boundary 40+TT1, and further dipping below 40 at time T6. Rather than immediately classify the patient's activity state as Inactive based solely on the boundaries associated with the definitions of FIG. 4A, episode detection may once again be applied to this transition. In this case, a transition threshold of TT2 is applied, such that signal 350 must drop below 40−TT2 before a boundary crossing is recognized. The transition threshold of TT2 is represented by arrow 358. This transition over the boundary of 40−TT2 occurs at time T7. At this time, a timer is used to measure a transition duration represented by arrow 360. If signal 350 remains below the level of 40−TT2 for a time period of at least the transition duration, an episode of the Inactive posture state will be detected.

In the instant case, signal 350 rises above the boundary of 40−TT2 before timer expiration occurs at time T8, as shown by arrow 360. Therefore, an episode of the patient being in the Inactive activity state is not detected. However, at time T8, the signal once again crosses the boundary of 40−TT2. Therefore, a timer associated with the transition duration is again started, as indicated by arrow 362. This time, the activity state signal remains below the boundary of 40−TT2 for longer the transition duration, as indicated by arrow 362. Therefore at time T9, when the transition duration has elapsed, an episode of the Inactive activity state will be detected.

In the foregoing manner, a transition threshold and transition duration may be applied to activity detection. If desired, these values may be automatically selected based on the most-recently detected stable posture state (that is, the posture state from which the patient is transitioning), the next posture state (the posture state to which the patient is transitioning), or the specific transition that is occurring. Additionally or alternatively, these values may be selected based on whether the transition occurs in the upward or downward direction. Thus, for instance, the values TT1 and TT2, as represented by arrow 352 and 358, respectively, need not be the same even though these values are associated with a transition between the same two activity states of Inactive and Moderate Activity. Similarly, the two transition durations involved with this transition, as represented by arrows 354, 356 and arrows 360, 362 need not be the same when a signal trends upward versus downward. In yet another embodiment, a same transition threshold and duration may be selected for all transitions and may be the same regardless of direction of transition. The transition thresholds and durations available for use in the system may be stored in a data structure similar to that shown in FIG. 9 for use with dwell times. In this manner, various values may be available for use such that the transition threshold and duration that will be used at any given time may be automatically selected based on monitored system conditions.

In the embodiments of FIG. 13, the transition thresholds are relative values that are used to modify boundaries set forth in posture state definitions. For instance, in one embodiment provided above, the relative transition threshold value of 5 is added to the boundary of 40 that is used to define a posture state transition involving the posture state of Inactive. Instead of using this relative transition threshold value, in another embodiment, an absolute transition threshold value of 45 may be used instead. In this embodiment, the transition threshold is used as the boundary, rather than modifying a boundary provided by the posture state definition.

Transition thresholds and durations may be programmable, if desired. Such programming may be accomplished using a clinician programmer 20, or some other external programmer or external device. Alternatively, one or more such values may be pre-selected ("hardcoded") by a device manufacturer. If desired, in some or all situations, the transition threshold and/or transition duration may be set to 0, thus eliminating in full or in part, the use of episode detection for those situations.

Returning to the functional diagram of FIG. 6, it may be noted that episode detection logic 208 will only report episode detection if the transition threshold and transition duration conditions are met in a manner shown in FIG. 13. Thus, even though the signal provided by activity detection logic 100 meets the requirements specified by posture state definitions, an associated episode of activity may not be recognized until a later time. This helps ensure that responses are not initiated as a result of transitory posture states or signal fluctuations that occur for some other reason. Responses are only initiated once it has been established that the patient has indeed transitioned to a new activity state based on the requirements imposed by episode detection.

Logic similar to episode detector 208 may be used to receive the posture signals on interface 106. The episode detector may be used to determine a posture episode. This determination may be made, for instance, by considering whether a detected posture vector $V_{pt}$ enters within some predetermined distance of a defined posture vector and stays no more than this distance away from the defined posture vector for at least a period of time equal to a corresponding transition duration. In this manner, the use of episode detection may be applicable not only to detection of an activity, but may alternatively or additionally be used to detect posture episodes. This episode detection may be used instead of, or in addition to, M-of-N filter 202 when detecting posture.

Figure 14:
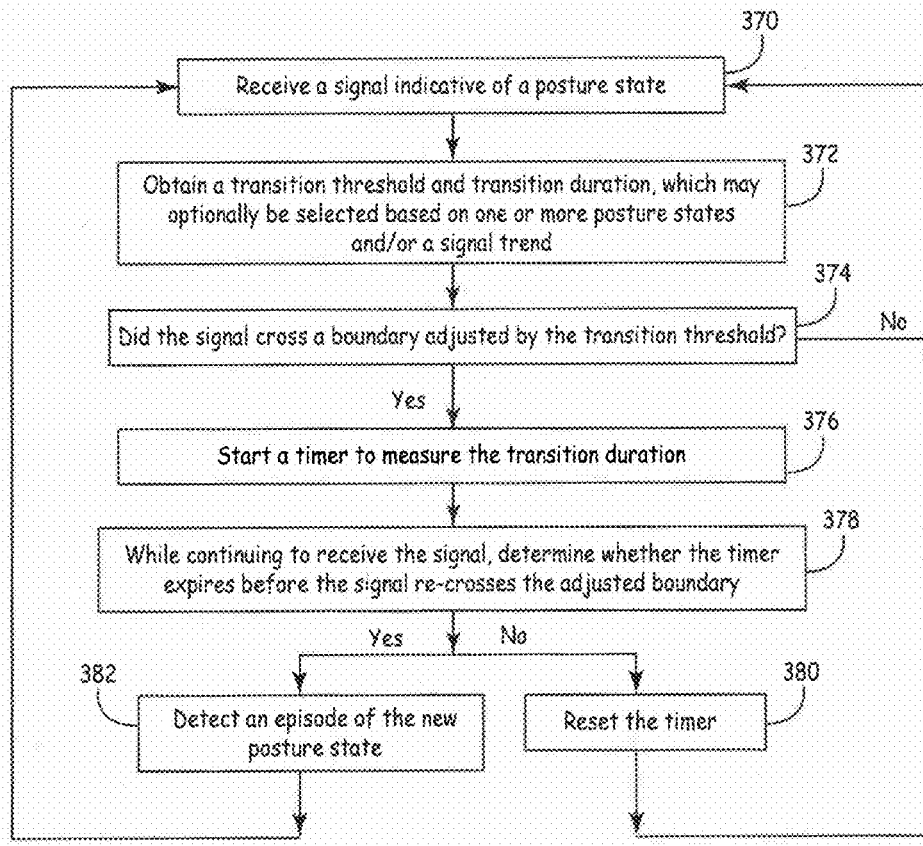
FIG. 14 is a flow diagram illustrating one embodiment of episode detection according to the disclosure.

FIG. 14 is a flow diagram illustrating one embodiment of episode detection according to the current disclosure. A signal indicative of a posture state is received (370). In the example FIG. 13, this signal is indicative of activity, but in another embodiment, a signal indication of posture may be used instead. For instance, one or more signals that are used as a detected posture vector $V_{pt}$ may be received and used for this purpose. Reception of the signal, as indicated by step 370, will be understood to be on-going during the remaining steps of FIG. 14, as occurs when signal samples are being continuously received, as shown in FIG. 13.

A transition threshold and transition duration may next be obtained (372). These values may be stored as system control parameters 58, for instance. The obtained values may be automatically selected, in one embodiment, based on one or more posture states. For instance, they may be selected based on a newly-assumed posture state to which the patient is transitioning, a most-recent stable posture state, or both. Alternatively or additionally, these values may be selected based on whether the signal indicative of the posture state is trending upward or downward.

Any one or more of the values that are obtained during step 372 may have been selected by a user such as a clinician. For instance, the clinician may utilize a user interface similar to those shown in FIGS. 11A and 11B to select one or more values to be used as the transition threshold and transition duration. Alternatively or additionally, one or more such values may be selected by the device manufacturer such that the values are "hardcoded".

Next, it is determined whether the received signal crossed a boundary defined by a posture state definition, wherein that boundary has been adjusted by the transition threshold (374). If not, processing returns to step 370. Otherwise, execution continues to step 376, where a timer is started to measure a period of time equal to the transition duration. While continuing to receive the signal (e.g., as regularly-received signal samples), it is determined whether the timer expires before the signal re-crosses the adjusted boundary (378). If the timer does expire before this happens, an episode of the new posture state is detected (382). This episode detection may be used to further classify the patient's posture, as shown in FIG. 6. If episode detection is used to further process a signal provided by posture state classifier 204, this episode detection may be used to prevent a response from being initiated after a posture state re-classification occurs until an episode of that posture state is detected. Execution may then return to step 370 to repeat the process.

Returning to step 378, if an episode of the new posture state is not detected, processing continues to step 380, wherein the timer may be reset, and processing may then return to step 370. In this case, the posture state re-classification that most recently occurred will not be used to initiate a response.

In the foregoing manner, episode detection may be used to impose a delay between the time a posture state transition is first detected, and the time that transition is used to classify a posture state and initiate a response. This delay may be used alone, or in conjunction with dwell times, to ensure that responses are not taken to posture states that are assumed in only a transitory manner. Thus, in one embodiment, dwell times may be set to zero, and episode detection may alone be used to impose the delay. In another embodiment, both dwell times and episode detection may be utilized for this purpose. According to still another approach, dwell times alone may be utilized, with transition durations and transition thresholds being set to zero.

Yet another technique for introducing stability into the system relates to use of the M-of-N filter. For purposes of this discussion, the M-of-N filter 202 of FIG. 6 will be referenced. This filter was applied to posture signals. However, it will be understood that this type of filter may be applied to the processing of activity states, and even to the processing of posture states that are indicated by posture state classifier 204.

According to one embodiment, M-of-N filter 202 maintains a buffer of a patient's N most recent posture classifications generated by posture classifier 200. In particular, this buffer stores the posture indication most recently provided by posture classifier 200, as well as the N−1 posture indications that were most recently provided before this by posture classifier 200. The M-of-N filter 202 then determines whether M of these N stored postures is a same posture. If so, an indication of this posture (which may be referred as the "M-of-N posture") is provided by M-of-N filter 202 to posture state classifier 204 on interface 206. If M of the most recent N postures is not a same posture, M-of-N filter 202 may, in one embodiment, provide an indication on interface 206 that no valid M-of-N posture was detected. Alternatively, when no M-of-N posture is detected, M-of-N filter 202 may instead repeat the indication of whichever posture was the last M-of-N posture to be detected by M-of-N filter. This latter embodiment is exemplified in the illustration of FIG. 15.

Figure 15:
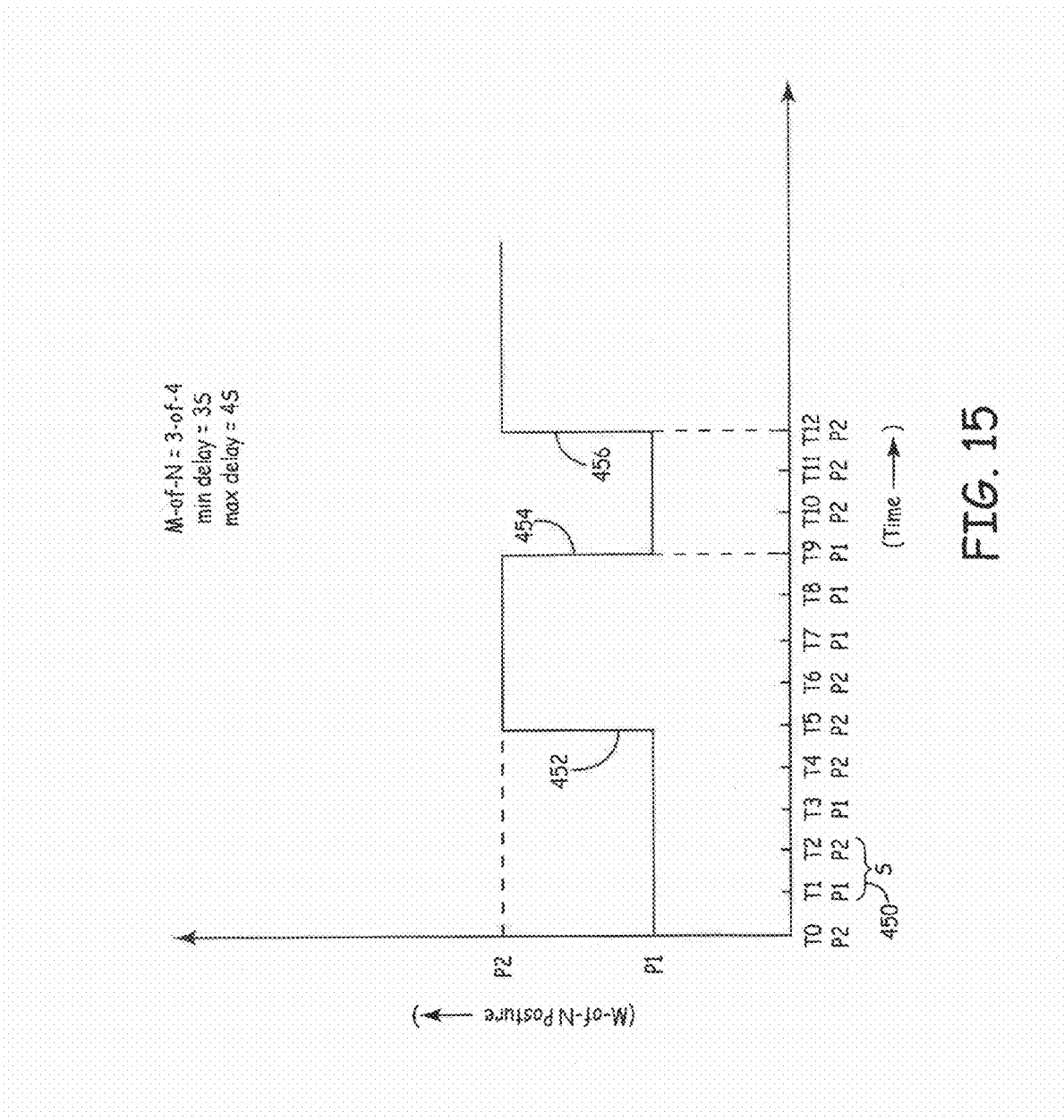
FIG. 15 is a timing diagram illustrating use of an M-of-N filter according to one embodiment of the disclosure.

FIG. 15 is a timing diagram illustrating use of an M-of-N filter according to one embodiment of the current disclosure. Assume this M-of-N filter is set to require that three out of the past four posture indications provided by posture classifier 200 must be the same posture for a posture indication to be provided on interface 206. Assume further that at time T0, M-of-N filter 202 is providing an indication of posture P1 on interface 206 to indicate this was the most-recently detected M-of-N posture. This is as shown on the Y axis of this graph. Also at time T0, it will be assumed the posture classifier 200 provides an indication of posture P2 on interface 201 to M-of-N filter 202. Such posture indications provided by posture classifier 200 are shown along the X axis of the graph in correspondence with time.

At regular time intervals having a period S 450, additional posture indications are provided on interface 201 to M-of-N filter 202. For instance, at times T1, T2, T3, and T4, the indications of postures P1, P2, P1, and P2, respectively, are provided on this interface, as shown along the X axis. As a result, at time T4, two out of the last four postures were an indication of posture P1, and the remaining two out of the four postures were an indication of posture P2. Thus, the requirement of three of the last four postures being the same posture was not fulfilled. For this reason, in this embodiment, M-of-N filter 202 continues to provide the indication of the previous M-of-N posture, which is assumed to be posture P1 in this example.

At time T5, another indication is received that identifies posture P2. As a result, three of the last four posture indications received from the posture classifier identify posture P2. Therefore, the M-of-N filter now provides an indication of posture P2 on interface 206, as shown by transition 452.

At times T6, T7, T8, and T9, the posture indications received by the M-of-N filter from posture classifier 200 on interface 201 are P2, P1, P1, and P1, respectively. The posture indicated by M-of-N filter 202 will not revert back to posture P1 until three of the last four posture indications identifies posture P1. This occurs at time T9, as shown by transition 454.

In a similar manner, the posture indicated by M-of-N filter 202 will not again indicate posture P2 until three of the last four posture indications received from posture classifier 200 are posture P2, as occurs at time T12, as illustrated by transition 456.

In the foregoing manner, the M-of-N filter 202 inserts a delay between the time posture classifier 200 first identifies a posture change, and the time this posture change becomes eligible to result in a re-classification of the patient's posture state. For a sample time of S 450, the minimum delay will be 3S. This occurs when three samples in succession are received that are indicative of the new posture indication. The maximum delay will be 4S, which occurs when three samples are received indicating the new posture, but these samples are included in a sequence of four samples that also includes one sample of a different posture.

Thus, the selection of "M" and "N" can affect the amount of delay, as well as the amount of variation between maximum and minimum delay times, that will occur between the time posture classifier 200 provides a sample indicating a new posture and the time that new posture is available to posture state classifier 204 to perform posture state classification. The values "M" and "N" may be programmable. In one embodiment, these values may be determined based on the current posture state data 55, or they may be based on the last M-of-N posture indicated by the M-of-N posture filter 202. Alternatively or additionally, these values may be determined based on some other variable condition within the system, such as a monitored physiological signal (e.g., blood pressure, heart rate, blood oxygen levels, etc.).

In one embodiment, "M" and "N" may be selected based on the posture to which the patient may be transitioning. For example, in one embodiment, whenever two of the last three posture indications are of a posture other than the last-detected M-of-N posture, that different posture may be used to re-select "M" and "N". This may be illustrated by returning to FIG. 15.

Assume at time T0, "M" and "N" are set to "3" and "4" according to the foregoing discussion. Also, at time T0, the M-of-N posture is "P1", as indicated along the Y axis of the graph. At time T2, two of the last three postures indicate "P2". Thus, according to the alternative embodiment, the posture of P2 is used at time T2 to re-select "M" and "N". This re-selection may be performed by referencing system control parameters 58, for instance, which may be stored within memory 36. Assume further that the new values for M and N that are to be used for the potential new posture of P2 coincidentally happen to be 2 and 3, respectively. This alternative embodiment will result in M-of-N filter 202 providing an indication of P2 at time T2, since two of the last three postures received from posture classifier 200 were P2, satisfying the requirements of the M-of-N filter. In another example, either M or N could be increased rather than decreased, or one or both of these values could remain the same based on the potential new posture P2. In this manner, the values used to determine how M-of-N filter 202 operates may be selected based on a posture to which the patient may potentially be transitioning.

In yet another embodiment, the specific transition may be used to select the values of M and N. In this case, the previous M-of-N posture, as well as the potentially-new posture (e.g., the posture indentified by the last two or three posture indications) will be used in combination to identify the specific transition. This transition may be used to select the values for the M-of-N posture. Transition-specific values for M and N may be stored along with system control parameters 58 in memory, or stored in some other data structure and/or storage device.

According to a variation of the foregoing, the value of N may be selected based on the last-detected M-of-N posture. After a majority of the N signals are received that identify a new posture, this new posture may be used to select the value for M.

Using any of the foregoing mechanisms, the last-detected M-of-N posture indicated by the M-of-N posture filter 202, the potentially new M-of-N posture indicated by the M-of-N posture filter, or both, may be used to determine the values for M and N. Alternatively, current posture state data 55, or some other monitored condition within the system, may be used for this purpose. The one or more values for M and N that are available for use in the system may be stored in a data structure similar to that shown in FIG. 9 for use with dwell times. In this manner, various values may be available for use, with the values used at any particular time being automatically selected based on monitored system conditions.

As discussed above, although the M-of-N filter 202 is illustrated as being used to provide an M-of-N posture, it may likewise be used instead of, or in addition to, episode detection 208 to determine an M-of-N activity state. For instance, after an activity state classification is made using episode detection 208, an M-of-N filter may be used to process this activity classification to obtain an M-of-N activity classification to provide to posture state classifier 204. Alternatively, the M-of-N filter may replace episode detection 208 to determine an M-of-N activity state classification to provide to posture state classifier 204. In yet another embodiment, an M-of-N filter may be used to process the posture state classifications provided by posture state classifier 204. This inserts additional processing steps to process the classification provided by posture state classifier 204 before that classification is provided to dwell time logic 214.

In the foregoing manner, an M-of-N filter may be used to classify postures, activity states, and/or posture states. If multiple such filters are employed for these various purposes, the values for M and N may be different for the various filters. Moreover, if the values for M and/or N are to be selected based on monitored conditions, the conditions that are used to select the values for M and/or N may be different for the various filters.

Figure 16:
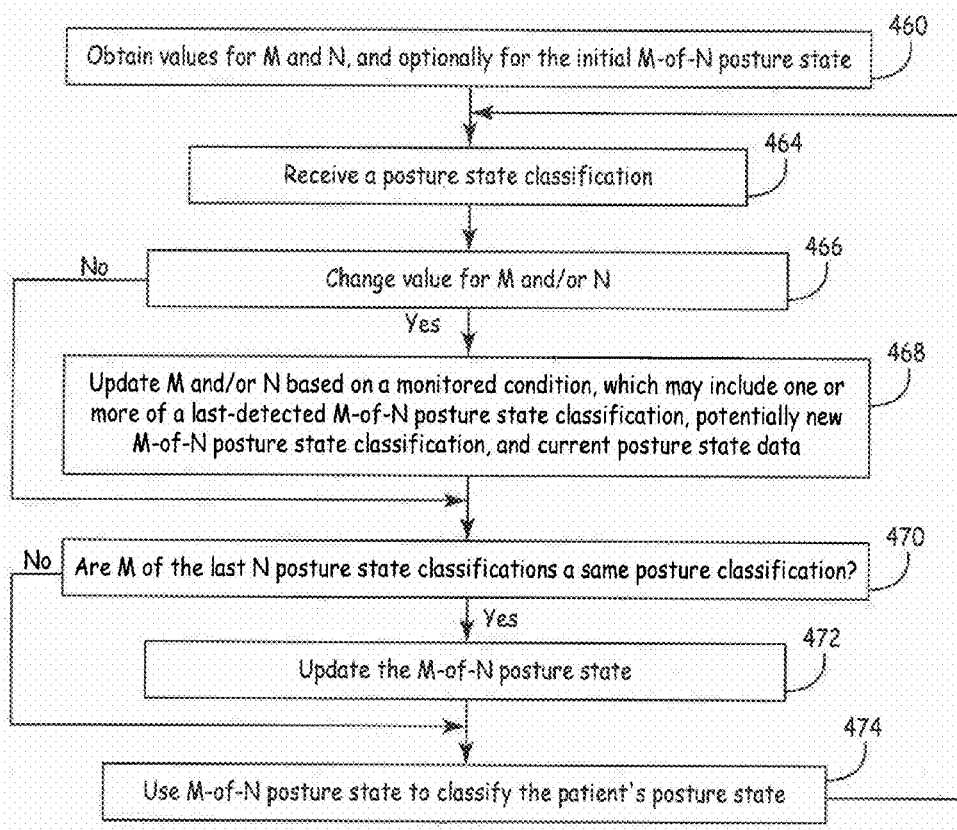
FIG. 16 is a flow diagram of an M-of-N filter according to one embodiment of the disclosure.

FIG. 16 is a flow diagram illustrating use of an M-of-N filter according to one embodiment. This flow diagram will be described generally based on use of an M-of-N filter to determine an M-of-N posture state, where the posture state may be based on posture, activity or both. Thus, this description may be applied to use of the M-of-N filter for any of the three embodiments discussed above involving posture, activity state, and posture state classification.

First, initial values for M and N may be determined (460). This step may optionally involve obtaining an initial value for the M-of-N posture state. One or more of these values may be hard-coded, as determined by a device manufacturer. Alternatively, one or more of these values may be programmable, as established by a user such as a clinician. In one embodiment, these values may be periodically automatically adjusted based on one or more monitored system conditions, as described below.

A posture state classification may next be received (464). In one embodiment, this posture state classification is based on operation of at least one of posture classifier 200, activity classifier 207, and posture state classifier 204.

Next, it may be determined whether the values for M and/or N are to be changed (466). This step may be eliminated in an embodiment wherein these values are hard-coded, or wherein these values do not change during the posture state classification process. In another embodiment, this step may be placed at a different point in the posture classification process.

If the values of M and/or N are not to be changed, execution continues to step 470. Otherwise, new values may be obtained for M and/or N (468). As discussed above, these values may be selected based on current posture state data 55, on the last-detected M-of-N posture state, on a potentially new M-of-N posture state, on both the last-detected and potentially-new M-of-N posture state (that is, the potential transition involving the M-of-N posture state), and/or based on some other monitored condition within the system.

At step 470, it is determined whether M of the last N classified posture states are the same posture state. If so, the M-of-N posture state is updated to reflect the posture state for which M of the last N posture states were the same (472). The M-of-N posture state may then be used to classify the patient's posture state 474. Processing may then return to step 464 to receive another posture state classification. If, in step 470, M of the last N posture state classifications are not a same posture classification, processing continues to step 474, wherein no update occurs such that the previous value for the M-of-N posture state is used to classify the patient's posture state.

In the foregoing manner, dwell time logic 214, episode detection 210, and/or M-of-N filter may be used in classifying posture states involving postures and/or activity states. In all three cases, this logic is used to introduce stability into the system in a similar manner. Dwell times are used to ensure that a patient remains in a posture state some predetermined period of time before some corresponding action is taken. Episode detection is used to ensure that for a posture state change to be recognized, a sensed signal involving posture or activity crosses a predetermined boundary that has been adjusted by the transition threshold, and further to ensure that no re-crossing of this boundary occurs during the transition duration. Finally, an M-of-N filter may be used to ensure that a posture state change is not recognized until a new posture and/or activity state is reliably recognized during a time period that will be determined by the selection of M and N. These three types of mechanisms, which may be used alone or in conjunction with one another, ensure that actions will not be initiated as a result of transitory posture and/or activity changes.

As previously discussed, any of the functions described above may be implemented in hardware, firmware, software or any combination thereof. The various parameters used to control operation of these functions may be hard-coded, programmable, or some combination thereof. Additionally or alternatively, one or more of the parameters may be automatically periodically re-selected within the system based on monitored conditions, including current posture state data 55 and/or other conditions.

Those skilled in the art will contemplate many alternative embodiments for the techniques and mechanisms described herein. For instance, the functional block diagram of FIG. 6 illustrates a two-tier system wherein a posture classifier 200 is used to classify posture, an activity classifier 207 is employed to classify activity state, and a posture state classifier 204 is used to classify posture state based on at least one of the posture classification and the activity state classification. In another embodiment, this two-tier system may be implemented as a single tier such that the posture state classifier receives posture signals (e.g., as from interface 106 of FIG. 6) and/or activity signals (e.g. as from interface 102) and compares these received signals to the posture state definitions to classify a posture state involving at least one of the posture and activity state. In this embodiment, any one or more of episode detector 208, M-of-N filter 202, and dwell time logic 214 may be used to perform this posture state classification, and/or to determine whether a particular response should be initiated as a result of the posture state classification.

As stated above, any of M-of-N filter 202, episode detector 208, and dwell time logic 214 may be adapted for, and used to perform, posture classification, activity state classification and/or posture state classification that involve posture and activity state classifications. As such, the various functional blocks of the various figures may be re-arranged and re-partitioned. Thus, it will be appreciated that many embodiments may be contemplated by those skilled in the art, and those described herein are merely exemplary, with the scope of the invention to be defined by the Claims that follow.

What is claimed is:

1. A medical device system, comprising:
a sensor configured to sense at least one signal indicative of a posture state of a living body;
posture state detection logic configured to classify the living body as being in a posture state based on the at least one signal and to determine whether the living body is classified in the posture state for at least a predetermined period of time; and
response logic configured to initiate a response as a result of the living body being classified in the posture state, the response being initiated only after the living body has maintained the classified posture state for at least the predetermined period of time.

2. A medical device system, comprising:
a sensor configured to sense at least one signal indicative of a posture state of a living body;
posture state detection logic configured to classify the living body as being in a posture state based on the at least one signal and to determine whether the living body is classified in the posture state for at least a predetermined period of time;
response logic configured to initiate a response as a result of the living body being classified in the posture state, the response being initiated only after the living body has maintained the classified posture state for at least the predetermined period of time; and
a therapy delivery module configured to deliver therapy to the living body, and wherein the response is a change in the therapy delivered by the therapy delivery module.

3. The system of claim 2, wherein the posture state detection logic comprises at least one of a posture classifier configured to classify the posture of the living body and an activity classifier configured to classify the activity state of the living body, and wherein the classification of the living body as being in a posture state is based on at least one of the posture classification and the activity state classification.

4. The system of claim 2, wherein the posture state detection logic comprises dwell time logic having one or more timers, each configured to measure a respective dwell time that commences at the time the living body is classified in the posture state; and
wherein upon expiration of each of the one or more timers, the response logic initiates a respective response as a result of the body being classified in the posture state only if the living body has not exited the posture state during the respective dwell time.

5. The system of claim 2, wherein the posture state detection logic comprises dwell time logic configured to automatically select a dwell time as the predetermined period of time, selection being based on the posture state in which the living body is classified.

6. The system of claim 5, wherein the dwell time logic is further configured to select the dwell time based on a posture state in which the living body was previously classified.

7. The system of claim 2, wherein the posture state detection logic comprises dwell time logic configured to automatically select a dwell time as the predetermined period of time, selection being based on at least one of a type of the response and a type of change in the response.

8. The system of claim 2, further comprising a user interface configured to allow a user to select the predetermined period of time.

9. The system of claim 2, wherein at least one of the sensors, the posture state detection logic and the response logic are implantable in the living body.

10. The system of claim 2, wherein the posture state detection logic comprises an M-of-N filter that indicates that the living body is in the posture state only if M of a most-recent N posture states in which the living body was classified are a same posture state.

11. The system of claim 10, wherein at least one of M and N are automatically selected based on at least one of the posture state in which the living body is classified and a posture state in which the living body was previously classified.

12. The system of claim 10, wherein at least one of M and N are selectable by a user.

13. The system of claim 2, wherein the posture state detection logic comprises an episode detector that detects a posture state episode based on a definition of the posture state, and a transition threshold that adjusts a boundary of the definition.

14. The system of claim 13, wherein the episode detector automatically selects the transition threshold based on a direction in which the at least one signal crosses the adjusted boundary.

15. The system of claim 13, wherein the predetermined period of time is a transition duration, and wherein the episode detector classifies the living body as being in the posture state if the at least one signal crosses the adjusted boundary and does not re-cross the adjusted boundary for at least the transition duration.

16. The system of claim 2, wherein the sensor is a three-axis accelerometer.

17. The system of claim 2, wherein the therapy delivery module is configured to deliver electrical stimulation to the living body.

18. The system of claim 2, wherein the response logic initiates a notification as a result of the living body being classified in the posture state.

19. The system of claim 2, wherein the response logic initiates storing of data as a result of the living body being classified in the posture state.

20. A medical system to provide therapy to a living body, comprising:
a sensor;
posture state detection logic configured to receive at least one signal from the sensor and to employ the at least one signal to classify a posture state of the living body;
a therapy module configured to control the therapy provided to the living body based on the classification; and
one or more processors configured to determine whether, after the living body is classified in a posture state, the living body maintains the posture state for a predetermined period of time, and wherein the therapy module is further configured to adjust the therapy in response to the posture state if the living body maintains the posture state for the predetermined period of time, and otherwise, to allow the therapy to remain unchanged.

21. The system of claim 20, wherein at least one of the sensor, posture state detection logic, one of the one or more processors and therapy module are implantable within the living body.

22. The system of claim 21, wherein the sensor is a three-axis accelerometer.

23. The system of claim 21, further comprising dwell time logic configured to automatically adjust the predetermined period of time based on the posture state in which the living body is classified.

24. The system of claim 21, wherein the dwell time logic automatically selects the predetermined period of time based on whether levels of the therapy will increase or decrease in response to the posture state.

25. The system of claim 20, further comprising a user interface configured to allow a user to select the predetermined period of time.

26. The system of claim 20, wherein the posture state detection logic classifies the posture state based on one or more posture state definitions defined by a user.

27. The system of claim 20, wherein the posture state detection logic comprises an M-of-N filter configured to determine whether M of the last N posture state classifications is a same posture state, and if so, to provide an indication to allow the therapy module to adjust the therapy in response to the posture state, and otherwise, to allow the therapy to remain unchanged.

28. The system of claim 27, wherein the predetermined period of time is determined by selection of at least one of M and N.

29. The system of claim 20, wherein one or more posture state definitions are created to classify the posture state of the living body, wherein the posture state detection logic comprises an episode detector configured to adjust a boundary of a posture state definition to determine whether an episode of the posture state has been detected, and if so, to provide an indication to allow the therapy module to adjust the therapy in response to the posture state, and otherwise, to allow the therapy to remain unchanged.

30. The system of claim 29, wherein the boundary is automatically adjusted by an amount determined by whether the at least one signal is trending upward or trending downward.

31. The system of claim 29, wherein the boundary is automatically adjusted by an amount determined by at least one of the posture state and a posture state in which the living body was previously classified.

32. The system of claim 20, wherein the therapy module is configured to adjust therapy to a new target level over a therapy adjustment time according to a therapy adjustment function, wherein at least one of the therapy adjustment time and the therapy adjustment function is programmably selected.

33. A method, comprising:
receiving at least one signal from a sensor;
classifying a living body as being in any of multiple defined posture states based on the at least one signal; and
determining whether the living body is classified as remaining in a posture state for a predetermined period of time, and only if the living body is classified as remaining in the posture state for the predetermined period of time, automatically initiating via a response module a response that is determined based on the posture state.

34. A method, comprising:
receiving at least one signal from a sensor;
classifying a living body as being in any of multiple defined posture states based on the at least one signal;
determining whether the living body is classified as remaining in a posture state for a predetermined period of time, and only if the living body is classified as remaining in the posture state for the predetermined period of time, automatically initiating via a response module a response that is determined based on the posture state; and
delivering a therapy to the living body, and wherein the response involves changing the therapy being delivered based on the posture state.

35. The method of claim 34, further comprising:
automatically selecting the predetermined period of time based on the posture state;
employing a timer to measure the predetermined period of time; and
if the predetermined period of time elapses before the living body has exited the posture state, automatically initiating the response.

36. The method of claim 34, further comprising automatically selecting the predetermined period of time based on a type of the response.

37. The method of claim 34, further comprising automatically selecting the predetermined period of time based on a change in therapy that would result if the response were initiated.

38. The method of claim 34, further comprising receiving from a user at least one value identifying the predetermined period of time.

39. The method of claim 34, wherein determining whether the living body is classified in the same posture state comprises determining whether an episode of the posture state was detected for the living body, the episode being detected by adjusting a definition associated with the multiple defined posture states via a transition threshold, and determining whether the at least one signal satisfies the adjusted definition for a time period of not less than a transition duration.

40. The method of claim 39, further comprising:
monitoring one or more conditions of the living body; and
automatically selecting at least one of the transition threshold and the transition duration based on at least one of the monitored conditions of the living body.

41. The method of claim 34 wherein determining whether the living body is classified in the same posture state comprises determining whether an episode of an activity state was detected for the living body.

42. The method of claim 34, wherein determining whether the living body is classified in the same posture state comprises determining whether M out of the last N times the living body was classified as being in any of the multiple defined posture states, the living body was classified as being in a same one of the multiple defined posture states.

43. The method of claim 42, further comprising:
monitoring one or more conditions of the living body; and
automatically selecting at least one of N and M based on the monitored one or more conditions.

44. A non-transitory storage medium storing instructions executable by a processor to cause the processor to:
classify a living body as being in a posture state;
determine whether the living body remains in the posture state for at least a predetermined period of time, and only if the living body remains in the posture state for at least the predetermined period of time, automatically initiate a response that is determined based on the posture state, wherein the response is a change in therapy delivered to the living body.

45. The system of claim 20, further comprising a programmer configured to provide parameters to control the therapy provided by the therapy module.

46. The system of claim 45, wherein the programmer comprises at least one of the one or more processors.

47. The system of claim 2, wherein the posture state detection logic comprises a filter configured to determine whether the living body is classified in the posture state for at least the predetermined period of time.

48. The system of claim 2, wherein the posture state detection logic comprises programmable logic configured to determine whether the living body is classified in the posture state for at least the predetermined period of time.

49. The method of claim 34, wherein determining whether the living body is classified as remaining in a posture state for a predetermined period of time comprises filtering the at least one signal.

50. The method of claim 34, wherein determining whether the living body is classified as remaining in a posture state for a predetermined period of time comprises processing the at least one signal with programmable logic.

51. The system of claim 2, wherein the posture state comprises a posture.

52. The system of claim 2, wherein the posture state detection logic is configured to classify the living body as being in any one of multiple defined posture states, wherein each of the multiple defined posture states is associated with one or more therapy parameter values and wherein the therapy delivery module is configured to deliver therapy using therapy parameter values associated with a posture state in which the living body is most-recently classified.

53. The system of claim 2, wherein the predetermined period of time is automatically selected based on monitored system conditions.

54. The system of claim 2, wherein the predetermined period of time is programmable.

55. The method of claim 34, wherein classifying a living body as being in any of multiple defined posture states based on the at least one signal comprises classifying a living body as being in any of multiple defined postures based on the at least one signal.

56. The method of claim 34, wherein delivering a therapy to the living body comprises delivering a therapy to the living body using therapy parameters associated with a posture state in which the living body is classified.

57. The method of claim 34, further comprising automatically re-selecting the predetermined period of time.

* * * * *